(12) United States Patent
Dahlman et al.

(10) Patent No.: US 11,116,729 B2
(45) Date of Patent: Sep. 14, 2021

(54) DRUG DELIVERY SYSTEMS CONTAINING OXIDIZED CHOLESTEROLS

(71) Applicant: Georgia Tech Research Corporation, Atlanta, GA (US)

(72) Inventors: James Dahlman, Atlanta, GA (US); Kalina Paunovska, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 16/743,452

(22) Filed: Jan. 15, 2020

(65) Prior Publication Data

US 2020/0246273 A1 Aug. 6, 2020

Related U.S. Application Data

(60) Provisional application No. 62/793,671, filed on Jan. 17, 2019.

(51) Int. Cl.
*A61K 9/51* (2006.01)
*C12N 15/113* (2010.01)

(52) U.S. Cl.
CPC .......... *A61K 9/5123* (2013.01); *A61K 9/5146* (2013.01); *C12N 15/113* (2013.01)

(58) Field of Classification Search
CPC ........... A61K 9/127; A61K 9/51; A61K 31/00
See application file for complete search history.

(56) References Cited

U.S. PATENT DOCUMENTS

| | | | |
|---|---|---|---|
| 8,114,845 B2 | 2/2012 | Langermann et al. | |
| 8,609,089 B2 | 12/2013 | Langermann et al. | |
| 8,709,416 B2 | 4/2014 | Langermann et al. | |
| 2015/0110857 A1 | 4/2015 | DeRosa et al. | |
| 2018/0153822 A1* | 6/2018 | Karve | A61K 38/1816 |

FOREIGN PATENT DOCUMENTS

| | | | | |
|---|---|---|---|---|
| WO | WO 2017/201333 A1 | 11/2017 | | |
| WO | WO 2018/170336 A1 | 9/2018 | | |
| WO | WO-2018170336 A1 * | 9/2018 | ........... | C12N 15/113 |

OTHER PUBLICATIONS

W. Zhang, et al."Targeted delivery of chemically modified anti-miR-221 to hepatocellular carcinoma with negatively charged liposomes," Int. J. Nanomed. 2015:10 4825-4836. (Year: 2015).*
Google scholar search hedgehog pathway_Dec. 15, 2020 (Year: 2020).*
Google scholar search C18PEG2000 (Year: 2020).*
International Search Report and Written Opinion dated Apr. 7, 2020 in International Application No. PCT/US2020/013639, in 8 pages.
Hajj et al., "Tools for translation: non-viral materials for therapeutic mRNA delivery", *Nature Reviews*, 2017, pp. 1-17, vol. 2, No. 17056.
Kolios et al., "Role of Kupffer cells in the pathogenesis of liver disease", *World Journal of Gastroenterology*, 12:7413 (2006).
Paunovska et al., "A Direct Comparison of in Vitro and in Vivo Nucleic Acid Delivery Mediated by Hundreds of Nanoparticles Reveals a Weak Correlation", *Nano Lett.*, 2018, pp. 2148-2157, vol. 18.
Paunovska et al., "Nanoparticles Containing Oxidized Cholesterol Deliver mRNA to the Liver Microenvironment at Clinically Relevant Doses", *Advanced Materials*, 2019, 1807748, in 7 pages.
Poisson et al., "Liver sinusoidal endothelial cells: Physiology and role in liver diseases", *Journal of Hepatology*, 66:212 (2017).
Rizk et al, "Update on the clinical utility of an RNA interference-based treatment: focus on Patisiran", *Pharmacogenomics and Personalized Medicine*, 10:267 (2017).
Second Written Opinion dated Dec. 4, 2020 in International Application No. PCT/US2020/013639, in 6 pages.
International Preliminary Report on Patentability dated Mar. 26, 2021 in International Application No. PCT/US2020/013639, in 6 pages.

* cited by examiner

*Primary Examiner* — Michael P Cohen
(74) *Attorney, Agent, or Firm* — Knobbe Martens Olson & Bear LLP

(57) ABSTRACT

Lipid nanoparticles and compositions thereof are disclosed herein. An exemplary nanoparticle composition includes an ionizable lipid, a phospholipid, a PEG-lipid, and a cholesterol modified with a hydroxyl group near the D-sterol ring. The disclosed nanoparticle compositions can target liver Kupffer cells and endothelial cells more preferentially than hepatocytes which should be beneficial in treating liver diseases in which dysfunctional Kupffer cells and endothelial cells are involved in disease pathogenesis.

19 Claims, 14 Drawing Sheets

DRUG DELIVERY SYSTEMS CONTAINING OXIDIZED CHOLESTEROLS

RELATED APPLICATION INFORMATION

This application claims priority to U.S. Ser. No. 62/793,671, filed Jan. 17, 2019. The foregoing is hereby incorporated herein by reference in its entirety.

STATEMENT REGARDING FEDERALLY SPONSORED RESEARCH

This invention was made with government support under 1RO1DE026941-01A1, T32GM008433, and T32EB021962 awarded by The National Institutes of Health. The government has certain rights in the invention.

TECHNICAL FIELD OF THE INVENTION

The invention is generally directed to drug delivery systems and methods of their use.

BACKGROUND OF THE INVENTION

The use of RNA to produce therapeutic proteins or to modify gene expression is a promising approach to treat diseases. There have been several advances in local and systemic mRNA delivery (K. A. Hajj, K. A. Whitehead, Nature Reviews Materials, 2, 17056 (2017)), However, low dose mRNA delivery to many cell types within the organ and tumor microenvironments remains challenging. Identifying nanoparticles that efficiently deliver therapeutic RNA to cells within certain microenvironments is difficult because nanoparticles tend to preferentially target specific cell types, for example, in the liver nanoparticles preferentially target hepatocytes. Additionally, nanoparticles that target specific cell types in a microenvironment are difficult to design, in large part because there is no high throughput method to study nanoparticle mRNA delivery in vivo.

This universal problem in nanomedicine slows the development of all RNA therapies since scientists are forced to perform high throughput nanoparticle assays in vitro, even though cell culture can be a poor predictor of delivery within a complex in vivo microenvironment (Paunovska, K. et al., Nano Letters, 18: 2148-2157 (2018)). In vivo mRNA delivery is affected by pulsatile blood flow, heterogenous vasculature, and clearance by the kidney, spleen, liver, lymphatics, and immune system. Barcoding technologies have quantified lipid nanoparticle (LNP) biodistribution, which is necessary, but not sufficient, for cytoplasmic nucleic acid delivery. More specifically, less than 3% of a drug that reaches a target cell can escape into the cytoplasm, and the genes that alter whether the nanoparticle escapes into the endosome are likely to vary with each cell type.

Therefore, there is a need for more effective nanoparticles to target specific cell in an organ or tumor microenvironment.

It is an object of the invention to provide compositions and methods for delivering therapeutic and prophylactic agents to various organ microenvironments.

It is another object of the invention to provide nanoparticle compositions for treating and preventing diseases, including liver disease.

SUMMARY OF THE INVENTION

Compositions for delivering nucleic acids to specific cells or tissue microenvironments are provided. It has been discovered that oxidized cholesterol can modify the tropism of nanoparticles. One embodiment provides a nanoparticle containing oxidized cholesterol. Another embodiment provides a lipid nanoparticle containing one or more oxidized cholesterols. An exemplary nanoparticle composition includes an ionizable lipid, a phospholipid, one or more PEG lipids, and an oxidized cholesterol. By using specific oxidized cholesterols, the tropism of a nanoparticle can be tuned to a desired cell type or tissue microenvironment.

Another embodiment provides nanoparticles, for example lipid nanoparticles containing cholesterols modified with a hydroxyl group near the D sterol ring can preferentially deliver cargo to non-hepatocytes within the liver. In one embodiment, the nanoparticle composition includes 3,6-bis({4-[bis(2-hydroxydodecyl)amino]butyl})piperazine-2,5-dione (CKK-E12), $C_{14}PEG_{2000}$ or $C_{18}PEG_{2000}$ and an oxidized cholesterol modified with a hydroxyl group near the D sterol ring. The oxidized cholesterol can be 20α-hydroxycholesterol, 6-keto-5α-hydroxycholesterol, 7α-hydroxycholesterol, 7β-hydroxycholesterol, 7-ketocholesterol, 7β,25-dihydroxylcholesterol, 27-hydroxycholesterol, 25-hydroxycholesterol, or combinations thereof.

Still another embodiment provides a nanoparticle composition having about 30 mol % to about 80 mol % ionizable lipid, about 5 mol % to about 55 mol % cholesterol, about 10 mol % to about 35 mol % phospholipid, and about 0 mol % to about 20 mol % PEG-lipid.

Another embodiment provides the disclosed nanoparticles loaded with cargo. The cargo can be a therapeutic or prophylactic agent. In one embodiment, the therapeutic agent is a nucleic acid including, but not limited to ssRNA, dsRNA, sgRNA, mRNA, shRNA, siRNA, miRNA, ssDNA, dsDNA, antisense DNA, or combinations thereof. The nanoparticles can have a diameter from about 20 nm to about 215 nm. In one embodiment, the nanoparticles can have a diameter from about 50 nm to about 100 nm.

Another embodiment provides a pharmaceutical composition containing one or more of the disclosed lipid nanoparticles and a pharmaceutically acceptable excipient.

Yet another embodiment provides a method of delivering a therapeutic or prophylactic agent to a subject in need thereof, by administering to the subject one or more of the disclosed lipid nanoparticle compositions loaded with a therapeutic nucleic acid, for example a nucleic acid encoding a therapeutic protein, or an inhibitory or enzymatic nucleic acid. The method can further include administering a second therapeutic agent. In one embodiment, the nanoparticles preferentially deliver cargo to cells in the liver.

Another embodiment provides a method of preventing or treating liver disease in a subject in need thereof, by administering to the subject one or more of the disclosed lipid nanoparticles in an amount effective to prevent or treat liver disease. The lipid nanoparticles can be administered to the subject at a dose of 0.05 mg/kg. The liver disease can be hepatic cancer, liver cirrhosis, non-alcoholic fatty liver disease, and alcohol-related liver disease.

DETAILED DESCRIPTION OF THE INVENTION

I. Definitions

Figure 1A:
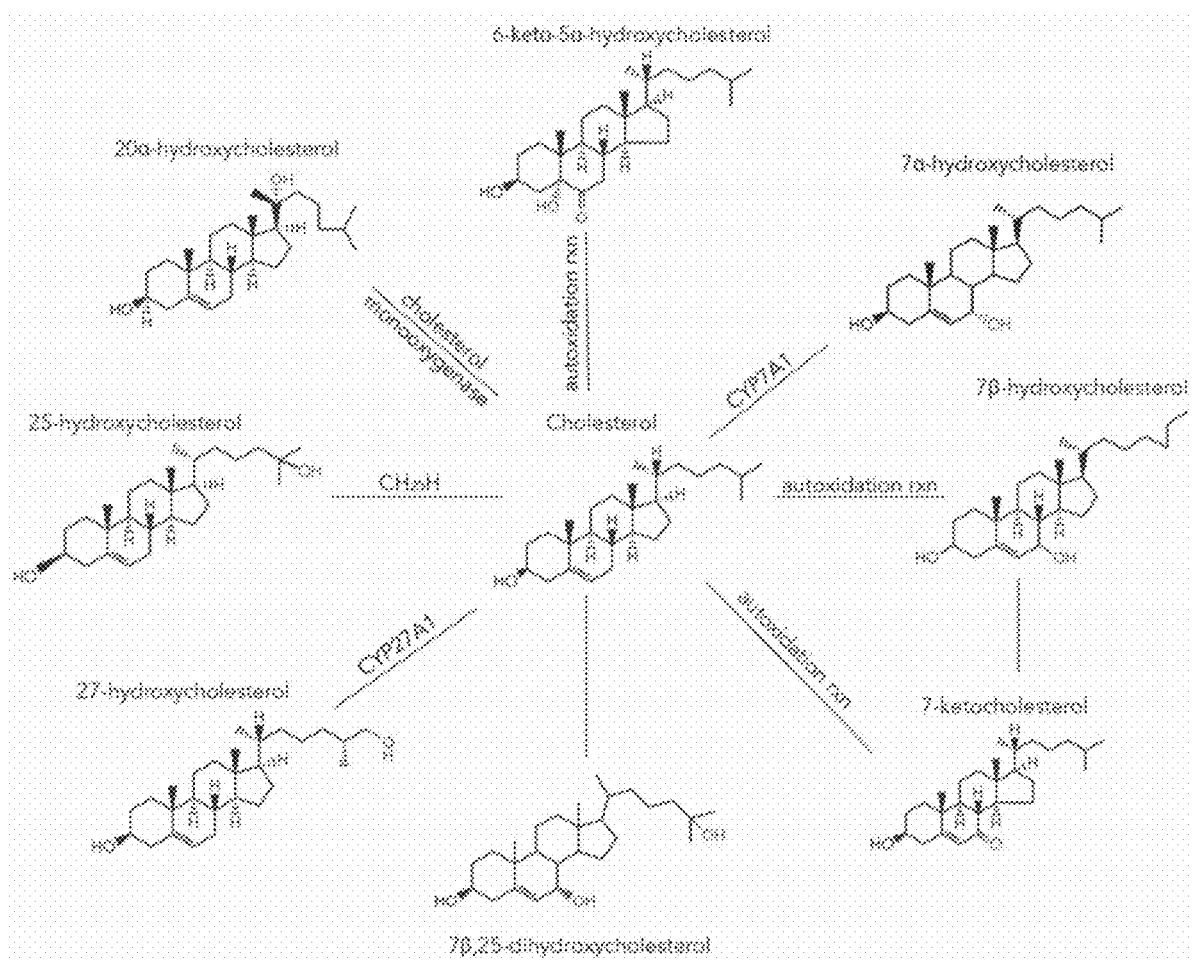
FIG. 1A is an illustration showing different sterol variations of cholesterol.
Figures 1B, 1C, 1D, 1E, 1F, 1G:
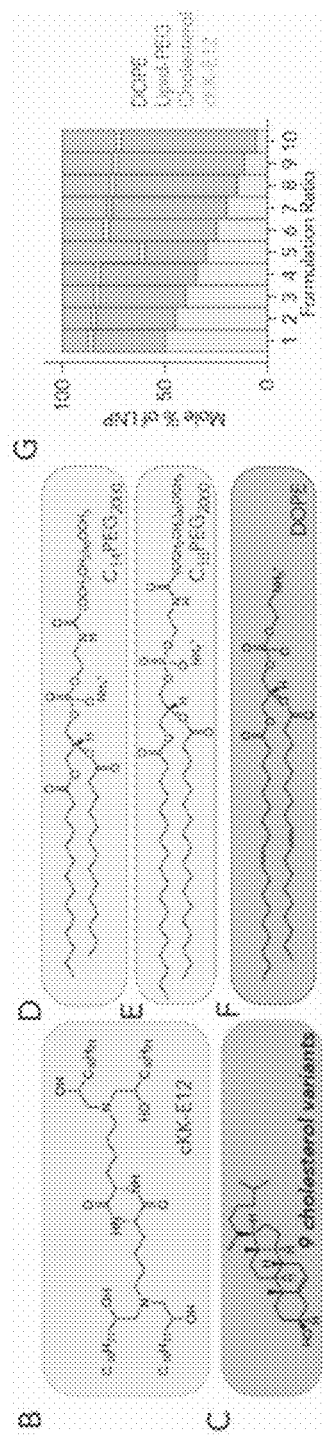
FIG. 1B is the chemical structure of the ionizable marker cKK-E12.
FIG. 1C is the chemical structure of cholesterol.
FIG. 1D is the chemical structure of $C_{14}PEG_{2000}$.
FIG. 1E is the chemical structure of $C_{18}PEG_{2000}$.
FIG. 1F is the chemical structure of DOPE.
FIG. 1G is a bar graph showing the formulation ratio of 10 different lipid nanoparticle designs. The graph shows the molar percent of DOPE, lipid-PEG, cholesterol, and cKK-E12 in each formulation. The X-axis represents the formulation ratio and the Y-axis represents the molar percent of each components of the lipid nanoparticles.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the nonlimiting group consisting of small interfering RNA (siRNA), microRNA (miRNA), Dicer-substrate RNA (dsRNA), small hairpin RNA (shRNA), mRNA, single-guide RNA (sgRNA), cas9 mRNA, and mixtures thereof.

The terms "polypeptide", "peptide", and "protein", may be used interchangeably to refer a string of at least three amino acids linked together by peptide bonds. Peptide may refer to an individual peptide or a collection of peptides. Peptides can contain natural amino acids, non-natural amino acids (i.e., compounds that do not occur in nature but that can be incorporated into a polypeptide chain), and/or amino acid analogs. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. Modifications may include cyclization of the peptide, the incorporation of D-amino acids, etc.

As used herein, "sterol" refers to an organic molecule that is a subgroup of the steroids. Sterols are also known as steroid alcohols. Sterols occur naturally in plants (known as phytosterols) and animals (known as zoosterols).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the terms "individual," "host," "subject," and "patient" are used interchangeably herein, and refer to a mammal, including, but not limited to, humans, rodents, such as mice and rats, and other laboratory animals.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "Kupffer cells" refer to resident liver macrophages. Kupffer cells function as scavenger cells responsible for removing particulate material from the portal circulation. Kupffer cells are also implicated in a number of pathologies of the liver including but not limited to viral hepatitis, steatohepatitis, alcoholic liver disease, intrahepatic cholestasis, activation or rejection of liver during liver transplantation, and liver fibrosis.

As used herein, "liver microenvironment" refers to the normal cells, molecules, and blood vessels that surround and feed the liver. Exemplary cells of the liver include but are not limited to sinusoidal endothelial cells (SEC), Kupffer cells (KC), hepatic stellate cells (HSC); and hepatocytes, as well as various immune cells.

The "inhibitory nucleic acid" refers to nucleic acids that inhibit the expression of specific genes or mRNA. Inhibitory nucleic acids include but are not limited to dsDNA, ssDNA, antisense DNA, siRNA, shRNA, miRNA, tasiRNA, and rasiRNA.

II. Lipid Nanoparticles

Effective, targeted delivery of biologically active substances such as small molecule drugs, proteins, and nucleic acids is a continuing challenge in the field of medicine. The delivery of nucleic acids specifically is made difficult by the relative instability and low cell permeability of nucleic acids. It has been discovered that lipid nanoparticles having modified cholesterol variants can more effectively deliver nucleic acids to specific tissues in the body. In one embodiment, lipid nanoparticles can be formulated by mixing nucleic acids with ionizable lipids, PEG-lipids, phospholipids, and a modified cholesterol. An exemplary lipid nanoparticle formulation can include the ionizable lipid-like material cKK-E12, PEG-lipids, 1,2-Dioleoyl-sn-glycero-3-phosphoethanolamine (DOPE), and one or more cholesterol variants. In one embodiment, the disclosed lipid nanoparticles preferentially target other cells of the liver microenvironment (i.e., Kupffer cells, endothelial cells, immune cells) over hepatocytes.

In one embodiment, the lipid nanoparticle formulation includes about 30 mol % to about 80 mol % ionizable lipid, about 10 mol % to about 35 mol % phospholipid, about 5 mol % to about 55 mol % modified cholesterol, and about 0 mol % to about 20 mol % PEG-lipid. In another embodiment, the lipid nanoparticle formulation include about 50 mol % ionizable lipid, about 15 mol % phospholipid, about 30 mol % modified cholesterol, and about 5 mol % PEG-lipid. In yet another embodiment, the lipid nanoparticle formulation include about 30 mol % ionizable lipid, about 20 mol % phospholipid, about 45 mol % modified cholesterol, and about 5 mol % PEG-lipid.

Lipid nanoparticle size can influence nanoparticle distribution. In one embodiment, the lipid nanoparticles can have a diameter from between about 20 to about 215 nm. The lipid nanoparticles can have a diameter that is about 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 210 nm, or 215 nm. In a preferred embodiment the nanoparticles have a diameter from between 50 nm to 100 nm.

A. Sterols

The disclosed lipid nanoparticles can include one or more sterols. In one embodiment, the sterols are cholesterols. The cholesterols can be modified, for example oxidized. Unmodified cholesterol can be acted upon by enzymes to form variants that are side-chain or ring oxidized (FIG. 1A). The cholesterols can be oxidized on the beta-ring structure or on the hydrocarbon tail structure. Exemplary cholesterols that are considered for use in the disclosed lipid nanoparticles include but are not limited to 25-hydroxycholesterol (25-OH), 20α-hydroxycholesterol (20α-OH), 27-hydroxycholesterol, 6-keto-5α-hydroxycholesterol, 7-ketocholesterol, 7β-hydroxycholesterol, 7α-hydroxycholesterol, 7β-25-dihydroxycholesterol, or combinations thereof. In one embodiment, side-chain oxidized cholesterol can enhance cargo delivery relative to other cholesterol variants. In a preferred embodiment, the modified cholesterol is 25-hydroxycholesterol (25-OH) or 20α-hydroxycholesterol (20α-OH).

Without being bound by any one theory, it is believed that lipid nanoparticles containing oxidized cholesterols can preferentially deliver cargo to other cells in the liver microenvironment instead of just to hepatocytes as is characteristic of existing lipid nanoparticles. Cholesterol is trafficked in lipoproteins using forward and reverse transport and trafficking to endothelial cells, hepatocytes, and macrophages may change with cholesterol structure in vivo. In addition, lipid nanoparticles and lipoproteins have similar size and composition, therefore lipid nanoparticles with cholesterol structures incorporated in them may be trafficked into cells similarly to lipoproteins.

B. Ionizable Lipids

In one embodiment, the disclosed lipid nanoparticles include an ionizable lipid. Ionizable lipids have a positive or partial positive charge at physiological pH. Exemplary ionizable lipids include but are not limited to 3,6-bis({4-[bis (2-hydroxydodecyl)amino]butyl})piperazine-2,5-dione (cKK-E12), 1-Linoleoyl-2-linoleyloxy-3-dmiethylaminopropane (DLin-2-DMAP), 1,2-Dilinoleylcarbanioyloxy-3-dimethylaniinopropane (DLin-C-DAP), 1,2-Dilmoleoyl-3-dimethylammopropane (DLm-DAP), 1,2-Dilinoleyloxy-N,N-dimethylaminopropane (DLin-DMA), 2,2-Dilinoleyl-4-dimethy laminomethy 1-[1,3]-dioxolane (DLin-K-DMA), 2,2-dilmoleyl-4-(2-dimethylaiiimoethyl)-[1,3]-dioxolane (DLin-KC2-DMA), (6Z,9Z,28Z,3 1Z)-heptatriaeonta-6,9, 28,3 1-tetraen-19-yl 4-(dimethylamino)butanoate (DLin-MC3-DMA), 1,2-dioieoyl-3-dimethylammonium propane (DODAP), N,N-dimethyl-(2,3-dioleyloxy)propylamine (DODMA), dioctadecylamidoglycyoucarboxysperrnine (DOGS), Spermine cholesterylcarbamate (GL-67), bis-guanidinium-spermidine-cholesterol (BGTC), 3β-(N—(N^N'-dimethylammoethanej-carbamoxlcholesterol (DC-Chol), N-t-butyl-N'-tetradecylamino-propionamidine (diC14-amidine), Dimethyldioctadecylammoniurnbromide (DDAB), N-(1,2-dimyristyloxyprop-3-yl)-N,N-dimethyl-N-hydroxyethyl ammonium bromide (DMR1E), N,N-dioleyl-N,N-dimethylammonium chloride (DODAC), Dioleyloxypropyl-3-dimethyl hydroxyethyl ammonium bromide (DOME), N-(1-(2,3-dioleyloxy3)propyl)-N-2-(spenninecarboxamido) ethyl)-N,N-dimethylamrnonium trifluoracetate (DOSPA), 2-dioleoy trimethyl ammonium propane chloride (DOTAP), N-(1-(2 3-dioleyloxy)propyl)-N N,N-trimethylammonium chloride (DOTMA) Aminopropyl-dimethyl-bis(dodecyloxy)-propanaminiumbromide (GAP-DLRIE), 1,2-dioleoyl-sn-3-phosphoethanolamine ("DOPE"), or combinations thereof. In a preferred embodiment, the ionizable lipid is cKK-E12.

C. PEG-Lipids

The lipid component of the disclosed nanoparticle compositions may include one or more PEG or PEG-modified lipids. Such species may be alternately referred to as PEGylated lipids. Inclusion of a PEGylating lipid can be used to enhance lipid nanoparticle colloidal stability in vitro and circulation time in vivo. A PEG lipid is a lipid modified with polyethylene glycol. In some embodiments, the PEGylation is reversible in that the PEG moiety is gradually released in blood circulation. Exemplary PEG lipids include but are not limited to PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, and mixtures thereof. For example, a PEG lipid may be PEG-c-DOMG, PEG-DMG, PEG-DLPE, PEG-DMPE, PEG-DPPC or a PEG-DSPE lipid.

In a preferred embodiment, the PEG lipid is $C_{14}PEG_{2000}$ or $C_{18}PEG_{2000}$.

D. Phospholipids

The lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties.

A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Nonnatural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Exemplary phospholipids include but are not limited to 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-0-octadecenyl-sn-glycero-3-phosphocholine (18:0 Diether PC), 1-oleoyl-2-cholesterylhemisuccinoy 1-sn-glycero-3-phosphocholine (OChemsPC), 1-hexadecyl-sn-glycero-3-phosphocholine (CI 6 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidy ethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE). In a preferred embodiment, the phospholipid is DOPE.

E. Cargo

In one embodiment, the disclosed lipid nanoparticle compositions include a therapeutic or prophylactic agent to a subject. The therapeutic or prophylactic agent can be included in the lipid nanoparticle as the cargo. Exemplary cargo that are traditionally delivered via nanoparticles include but are not limited to chemotherapeutic agents, cytotoxic agents, radioactive ions, small molecules, proteins, polynucleotides, and nucleic acids.

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

Representative nucleic acids include but are not limited to deoxyribonucleic acid (DNA), ribonucleic acid (RNA) including messenger mRNA (mRNA), RNAi-inducing agents, RNAi agents, miRNAs, antisense RNAs, asymmetrical interfering RNA (aiRNA), microRNA (miRNA), Dicer-substrate RNA (dsRNA), small hairpin RNA (shRNA), transfer RNA (tRNA) ribozymes, catalytic DNA, RNAs that induce triple helix formation, aptamers, vectors, Cas9/sgRNA, and plasmid DNA.

F. Pharmaceutical Compositions

Nanoparticle compositions may be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactics. Pharmaceutical compositions may further include one or more pharmaceutically acceptable excipients or accessory ingredients such as those described herein.

Pharmaceutical compositions including the disclosed lipid nanoparticles are provided. Pharmaceutical compositions containing the nanoparticles can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed nanoparticles, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed nanoparticles, generally dosage levels of 0.01 to 5 mg/kg of body weight daily are administered to mammals. More specifically, a preferential dose for the disclosed nanoparticles is 0.05 to 0.25 mg/kg. Generally, for intravenous injection or infusion, dosage may be lower.

In certain embodiments, the lipid nanoparticle composition is administered locally, for example by injection directly into a site to be treated. Typically, the injection causes an increased localized concentration of the lipid nanoparticle composition which is greater than that which can be achieved by systemic administration. The lipid nanoparticle compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein, including those containing lipid nanoparticles, are administered in an aqueous solution, by parenteral injection. The formulation may also be in the form of a suspension or emulsion. In general, pharmaceutical compositions are provided including effective amounts of a lipid nanoparticle, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

The lipid nanoparticles disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of lipid nanoparticles, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases, linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Use

Methods of using the disclosed lipid nanoparticles to deliver cargo to specific cells or organs are disclosed herein.

In some embodiments, the nanoparticles can deliver therapeutic or prophylactic agents to specific cells or organs in a subject in need thereof. In another embodiment, the disclosed lipid nanoparticles can be used to treat or prevent diseases in a subject in need thereof.

A. Methods of Delivering Cargo to Cells and Organs

Methods of delivering a therapeutic and/or prophylactic agent to a subject in need thereof are provided herein.

In some embodiments, the disclosed lipid nanoparticle composition may target a particular type or class of cells (e.g., cells of a particular organ or system thereof). For example, a nanoparticle composition including a therapeutic and/or prophylactic of interest may be specifically delivered to a mammalian liver, kidney, spleen, intestine, or lung. Specific delivery to a particular class of cells, an organ, or a system or group thereof implies that a higher proportion of nanoparticle compositions including a therapeutic and/or prophylactic are delivered to the destination (e.g., tissue) of interest relative to other destinations. In some embodiments, specific delivery may result in a greater than 2 fold, 5 fold, 10 fold, 15 fold, or 20 fold increase in the amount of therapeutic and/or prophylactic per 1 g of tissue of the targeted destination.

Another embodiment provides targeted or specific delivery of an mRNA that encodes a protein binding partner such as an antibody or functional fragment thereof, a scaffold protein, or a peptide, or a receptor on a cell surface. An mRNA may additionally or instead be used to direct the synthesis and extracellular localization of lipids, carbohydrates, or other biological moieties. Alternatively, other therapeutic and/or prophylactics or elements of a nanoparticle composition may be selected based on their affinity for particular receptors such that a nanoparticle composition may more readily interact with a target cell population including the receptors. For example, ligands may include, but are not limited to, members of a specific binding pair, antibodies, monoclonal antibodies, Fv fragments, single chain Fv (scFv) fragments, Fab' fragments, F(ab')2 fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

Targeted cells may include, but are not limited to, hepatocytes, epithelial cells, hematopoietic cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In one embodiment, the disclosed lipid nanoparticles target cells of the liver microenvironment, excluding hepatocytes. These cells can be liver endothelial cells, Kupffer cells, and immune cells.

In another embodiment, the disclosed lipid nanoparticles target cells of the immune system. Exemplary immune cells include but are not limited to granulocytes, mast cells, monocytes, macrophages, neutrophils, dendritic cells, natural killer cells, B cells, T cells, including cytotoxic T cells, T helper cells, and regulatory T cells.

B. Methods of Modulating an Immune Response

The disclosed lipid nanoparticles can be used to modulate immune responses in subjects in need of such treatment. In one embodiment, the disclosed lipid nanoparticles target immune cells in the microenvironment of a diseased organ, organ system, or in a tumor. The immune cells can be macrophages, more specifically Kupffer cells.

1. Immune Response Stimulation a. Therapeutic Strategies

Methods of inducing or enhancing an immune response in a subject are provided. Typically, the methods include administering a subject an effective amount of the disclosed lipid nanoparticles or a pharmaceutical composition including the disclosed lipid nanoparticle. The immune response can be, for example, stimulation of innate immunity at a disease or tumor sites, more specifically stimulation of Kupffer cells. Kupffer cells are the first macrophage population of the body to come in contact with bacteria, bacterial endotoxins and microbial debris derived from the gastrointestinal tract and transported to the liver via the portal vein.

Alternatively, the lipid nanoparticles can stimulate signal transduction through immune cell receptors and promote or enhance an immune response.

In some embodiments, the lipid nanoparticles can be used to block suppressive immune cells to tumor microenvironments. In another embodiment, the lipid nanoparticles can be used to inhibit, reduce, or block tumor metastasis. In some embodiments, the lipid nanoparticles can reduce or inhibit the activity of immune suppressive macrophages, reduce the production of cytokines such as IL-12 by M1 macrophages, reduce the differentiation of macrophages, reduce the number of macrophages, reduce the ratio of macrophages within an immune cell population, or reduce the survival of macrophages.

The methods can be used in vivo or ex vivo to inhibit, reduce, or block suppressive immune responses and thereby have a stimulating therapeutic effect. In some embodiments, the lipid nanoparticles is administered directly to the subject. In some embodiments, the lipid nanoparticles are contacted with cells (e.g., immune cells) ex vivo, and the treated cells are administered to the subject (e.g., adoptive transfer). The lipid nanoparticles can enable a more robust immune response to be possible. The disclosed compositions are useful to stimulate or enhance immune responses involving T cells by inhibiting, reducing or blocking suppressive immune signal transduction through T cell receptors.

b. Subjects to be Treated i. Treatment of Cancer

The disclosed compositions and methods can be used to treat cancer. Generally, the lipid nanoparticles are used to stimulate or enhance an immune response to cancer in the subject by administering to the subject an amount of the lipid nanoparticles. The method can reduce one or more symptoms of the cancer. In one embodiment, the disclosed lipid nanoparticles inhibit, block, or reduce the number of macrophages at the tumor site, thereby reducing tumor angiogenesis and suppression of antitumor immune cells.

Cancer cells acquire a characteristic set of functional capabilities during their development through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

ii. Treatment of Infections

The disclosed lipid nanoparticles can be used to treat infections and infectious diseases. Generally, the lipid nanoparticles are used to stimulate or enhance an immune response to infection in the subject. The disclosed lipid nanoparticles can stimulate macrophages, more specifically Kupffer cells of the liver. In one embodiment, the lipid nanoparticles inhibits, reduces, or blocks a suppressive immune signal transduction. In another embodiment, the lipid nanoparticles induces, promotes, or enhances an immune response by inducing, promoting, or enhancing signal transduction through immune cell receptors. The method can reduce one or more symptoms of the infection.

The infection or disease can be caused by a bacterium, virus, protozoan, helminth, or other microbial pathogen that enters intracellularly and is attacked, i.e., by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus, Escherichia coli, Acinetobacter baumannii, Pseudomonas aeruginosa* or *Mycobacterium*.

In some embodiments, the disclosed compositions are used to treat chronic infections, for example infections in which T cell exhaustion or T cell anergy has occurred causing the infection to remain with the host over a prolonged period of time.

Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus.

Because bacterial infections are cleared primarily by macrophages, an increase in macrophage activity would be therapeutically useful in situations where more rapid or thorough clearance of an infective bacterial agent would be beneficial to an animal or human subject. Thus, the disclosed compositions can be administered for the treatment of local or systemic bacterial infections.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria,*

*Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*.

Other microorganisms that can be treated using the disclosed compositions and methods include, bacteria, such as those of *Klebsiella, Serratia, Pasteurella*; pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*Mucor, Absidia*, rhizophus), *Sporothrix* (*schenkii*), *Blastomyces* (*dermatitidis*), *Paracoccidioides* (*brasiliensis*), *Coccidioides* (*immitis*) and *Histoplasma* (capsulatuma), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi*, etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia*, or *Trypanosoma*, etc.

2. Immune Response Inhibiting a. Therapeutic Strategies

Methods of reducing or inhibiting an immune response in a subject are provided. Typically the methods include administering a subject an effective amount of the disclosed lipid nanoparticles, or cells primed ex vivo with these nanoparticles. The immune response can be, for example, promoting or enhancing a suppressive immune response. In one embodiment, the disclosed compositions reduce, block, or decrease the activity of M1 macrophages or M1 macrophage signaling and decrease the production of cytokines such as IL-12 to provide an immune suppressive response.

In another embodiment, the lipid nanoparticles promote a suppressive immune response by inducing, promoting, or enhancing signal transduction through immune cell receptors.

The methods can be used in vivo or ex vivo as immune response-inhibiting therapeutic applications. Thus in some embodiments, the lipid nanoparticles are administered directly to the subject. In some embodiments, the lipid nanoparticles are contacted with cells (e.g., immune cells) ex vivo, and the treated cells are administered to the subject (e.g. adoptive transfer). In general, the disclosed lipid nanoparticles can be used for treating a subject having or being predisposed to any disease or disorder to which the subject's immune system mounts an overactive or inappropriate immune response. The agents can enable a less robust immune response to be possible. The disclosed compositions are useful to reduce or inhibit immune responses involving T cells.

b. Inflammatory Responses

The disclosed lipid nanoparticles can be used to treat inflammation. Generally, the agents are used to reduce or inhibit an immune response in the subject by administering to the subject an amount of the disclosed lipid nanoparticles. The method can reduce one or more symptoms of the inflammation. In inflammation can be acute, chronic, or persistent inflammation.

In some embodiments, the lipid nanoparticles slow down the immune system. For example, agent can be used to control hyper-inflammatory response causing damage healthy tissues. Accordingly, in some embodiments, the agents are administered to a subject undergoing a hyper-inflammatory response. In such cases, controlling excessive immune responses can be beneficial to the subject.

c. Inflammatory and Autoimmune Diseases/disorders

The disclosed lipid nanoparticles can also be used to treat inflammatory or autoimmune diseases and disorders. Representative inflammatory or autoimmune diseases/disorders include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments the inflammation or autoimmune disease is caused by a pathogen, or is the result of an infection.

C. Methods of Treating Liver Disease

The disclosed methods and compositions can be used to reduce, decrease, prevent or otherwise limit the initiation, development, progression, signs or symptoms of diseases and disorders of the liver. Dysfunctional liver endothelial cells, Kupffer cells, and other cells within the liver microenvironment cause more disease than hepatocytes. Historically, nanoparticles tend to preferentially target hepatocytes, not the other cells in the liver microenvironment.

Without being bound to any one theory, it is believed that the cholesterol modifications disclosed herein allow the lipid nanoparticles to more potently deliver cargo to cells in the liver microenvironment in vivo.

In one embodiment, the disclosed nanoparticles can be used for protein replacement therapies within the liver microenvironment.

Lipid nanoparticles can be administered locally or systemically in an effective amount to elicit a local or systemic response, for example, in order to treat or prevent diseases of the liver. In a preferred embodiment the one or more lipid nanoparticles are administered at a dose of 0.05 to 0.25 mg/kg body weight once weekly. In another embodiment, the nanoparticles are delivered twice a month, once a month, or less frequently. Exemplary liver diseases and disorders that can be treated by lipid nanoparticles are provided below.

1. Liver Cancer

The disclosed methods and compositions can be used to reduce, decrease, prevent or otherwise limit the initiation, development, progression, signs or symptoms of liver cancers. In some embodiments, the liver cancers to be treated are asymptomatic liver cancers. In some embodiments, the liver cancer has been identified by detection of diagnostic markers associated with the initiation, development or progression of liver cancers. In further embodiments risk factors for the development of liver cancers are used as a mechanism to identify subjects that can benefit from prophylactic treatment with the disclosed methods and compositions.

In one embodiment, the disclosed lipid nanoparticles can deliver chemotherapeutic agents to the liver to treat liver cancer and/or reduce tumor burden. In another embodiment, the disclosed lipid nanoparticles can deliver apoptotic agents to the liver to treat liver cancer and/or reduce tumor burden.

2. Liver Cirrhosis

The disclosed methods and compositions can be used to reduce, decrease, prevent or otherwise limit the initiation, development, progression, signs or symptoms of liver cirrhosis.

Liver cirrhosis is a disease in which liver cells become damaged and are replaced by scar tissue. Factors that contribute to cirrhosis include but are not limited to infectious diseases, alcohol abuse, recreational drug abuse and non-fatty liver diseases. Liver cirrhosis is associated with the development of liver cancer. Chronic infection with hepatitis C virus (HCV) has been recognized as an increased risk of Hepatocellular Carcinoma (HCC). Approximately 20% of HCV-infected individuals have diseases that progress to cirrhosis, and about 40% of these patients develop HCC after a mean of 10-15 years. Cirrhosis of the liver can also be caused by infection with Hepatitis B virus (HBV).

In one embodiment, the disclosed lipid nanoparticles can deliver therapeutics to the liver to treat symptoms of cirrhosis, or to halt the progression of the disease.

3. Fatty Liver Disease

The disclosed methods and compositions can be used to reduce, decrease, prevent or otherwise limit the initiation, development, progression, signs or symptoms of fatty liver disease. The fatty liver disease may be a result of alcohol abuse, which is a leading cause of cirrhosis in the United States.

The fatty liver disease may also be non-alcoholic fatty liver disease. Cirrhosis of the liver can be caused by non-alcoholic fatty liver disease, which is a condition in which people who consume little or no alcohol develop a fatty liver. Non-alcoholic fatty liver disease is common in obese people. People with a type of this disease known as non-alcoholic steatohepatitis (NASH) might go on to develop cirrhosis. Type 2 diabetes has been linked with an increased risk of liver cancer, especially in patients who also have other risk factors such as heavy alcohol use and/or chronic viral hepatitis. This risk may be increased because people with type 2 diabetes tend to be overweight or obese, which in turn can cause liver problems.

In some embodiments the disclosed lipid nanoparticles are used prophylactically. Accordingly, lipid nanoparticles can be administered daily in the absence of the symptoms or markers of liver disease, to promote general liver health and to prevent the development of liver disease in individuals who are at risk of liver diseases.

IV. Combination Therapies

The disclosed lipid nanoparticles can be administered to a subject in need thereof alone or in combination with one or more additional therapeutic agents. In some embodiments, the lipid nanoparticles and the additional therapeutic agent are administered separately, but simultaneously. The lipid nanoparticles and the additional therapeutic agent can also be administered as part of the same composition. In other embodiments, the lipid nanoparticles and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The lipid nanoparticles can be the first or the second therapeutic agent.

The lipid nanoparticles and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response or reduce or inhibit an immune response.

A. Increasing Immune Responses

1. Antimicrobials

For example, the disclosed lipid nanoparticles can be used in a preventive or prophylactic role in the treatment and prevention of disease as discussed above, and also in the context of severe trauma injuries like major burn, open bone fracture, accidental amputation or other wounds. Therefore, the disclosed lipid nanoparticles can be administered to the subject in combination with an antimicrobial such as an antibiotic, an antifungal, an antiviral, an antiparasitics, or essential oil.

In some embodiments, the subject is administered lipid nanoparticles and/or the antimicrobial at time of admission to the hospital to prevent further bacterial, fungal or viral complications. The antibiotic can target pathogens and the lipid nanoparticles can stimulate the immune system to provide an enhanced response to treat or prevent further infection or disease.

2. Chemotherapeutic Agents

The disclosed lipid nanoparticles can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

3. Other Immunomodulators a. PD-1 Antagonists

In some embodiments, lipid nanoparticles are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MEW) (see, for example, Freeman, Proc. Natl. Acad. Sci. U. S. A, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor.

Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., Clin. Cancer Res., 14:3044-3051 (2008).

Exemplary anti-B7-H1 (also referred to as anti-PD-L1) antibodies include, but are not limited to, those described in the following U.S. Pat. Nos. 8,383,796, 9,102,725, 9,273,135, 9,393,301, and 9,580,507, all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147, all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., Clinical Kidney Journal, 3(2):135-137 (2010), published online December 2009.

In other embodiments, the antagonist is a small molecule. A series of small organic compounds have been shown to bind to the B7-1 ligand to prevent binding to CTLA4 (see Erbe et al., J. Biol. Chem., 277:7363-7368 (2002). Such small organics could be administered alone or together with an anti-CTLA4 antibody to reduce inhibitory signal transduction of T cells.

4. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule.

Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke Crit Rev. Immunol. 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr−1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. Cancer Immunol. Immunother. 58:1219-1228 (2009). A similar result was observed in the HHD2 tumor model: adoptive transfer of CD4+CD25+ Treg after CTX pretreatment eliminated therapeutic response to vaccine (Taieb, J. J. Immunol. 176:2722-2729 (2006)).

Numerous human clinical trials have demonstrated that low dose CTX is a safe, well-tolerated, and effective agent for promoting anti-tumor immune responses (Bas, & Mastrangelo Cancer Immunol. Immunother. 47:1-12 (1998)).

The optimal dose for CTX to potentiate an anti-tumor immune response, is one that lowers overall T cell counts by lowering Treg levels below the normal range but is sub-therapeutic (see Machiels et al. Cancer Res. 61:3689-3697 (2001)).

In human clinical trials where CTX has been used as an immunopotentiating agent, a dose of 300 mg/m2 has usually been used. For an average male (6 ft, 170 pound (78 kg) with a body surface area of 1.98 m2), 300 mg/m2 is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. Cancer Res. 61:3689-3697 (2001), Hengst et al Cancer Res. 41:2163-2167 (1981), Hengst Cancer Res. 40:2135-2141 (1980)).

For larger mammals, such as a primate, such as a human, patient, such mg/m2 doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

B. Reducing Immune Responses

1. Immunosuppressive Agents

In some embodiments, the immune response, or inflammatory/autoimmune disease/disorder is treated by administering to the subject the disclosed lipid nanoparticles and a second agent that is an immune suppressant. Immunosuppressive agents include, but are not limited to antibodies against other lymphocyte surface markers (e.g., CD40, alpha-4 integrin) or against cytokines), fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e., Endoxan®, Cytoxan®, Neosar®, Procytox®, Revimmune™), methotrexate (MTX) (i.e., Rheumatrex®, Trexall®), belimumab (i.e., Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

The therapeutic agent can be a CTLA-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the therapeutic agent is a CTLA-4-Ig fusion protein known as belatacept. Belatacept contains two amino acid substitutions (L104E and A29Y) that markedly increase its avidity to CD86 in vivo. In another embodiment, the therapeutic agent is Maxy-4.

In another embodiment, the therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. Cyclophosphamide (CTX) is the primary drug used for diffuse proliferative glomerulonephritis in patients with renal lupus.

The therapeutic agent can be administered in an effective amount to reduce the blood or serum levels of anti-double stranded DNA (anti-ds DNA) auto antibodies and/or to reduce proteinuria in a patient in need thereof.

In another embodiment, the therapeutic agent increases the amount of adenosine in the serum, see, for example, WO 08/147482. For example, the second therapeutic agent can be CD73-Ig, recombinant CD73, or another agent (e.g., a cytokine or monoclonal antibody or small molecule) that increases the expression of CD73, see for example WO 04/084933. In another embodiment the therapeutic agent is Interferon-beta.

The therapeutic agent can be a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-18 IL-17, IL-6, IL-23, IL-22, IL-21, and MMPs. In another embodiment, the therapeutic agent is a small molecule that interacts with Tregs, enhances Treg activity, promotes or enhances IL-10 secretion by Tregs, increases the number of Tregs, increases the suppressive capacity of Tregs, or combinations thereof.

In some embodiments, the composition increases Treg activity or production. Exemplary Treg enhancing agents include but are not limited to glucocorticoid fluticasone, salmeteral, antibodies to IL-12, IFN-γ, and IL-4; vitamin D3, and dexamethasone, and combinations thereof.

In some embodiments, the therapeutic agent is an antibody, for example, a functions blocking antibody against a proinflammatory molecule such as IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. In some embodiments, the language "rapamycin compound" as used herein does not include FK506-like compounds.

2. Anti-Inflammatories

Other suitable therapeutic agents include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

EXAMPLES

Figures 6A, 6B:
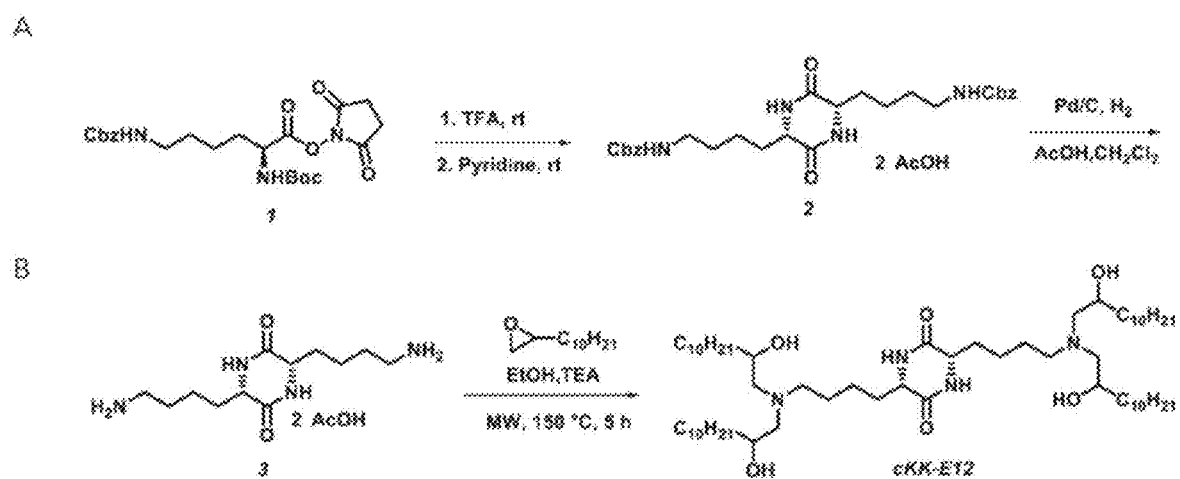
FIGS. 6A-6B are diagrams showing CKK-E12 synthesis.
Figure 6C:
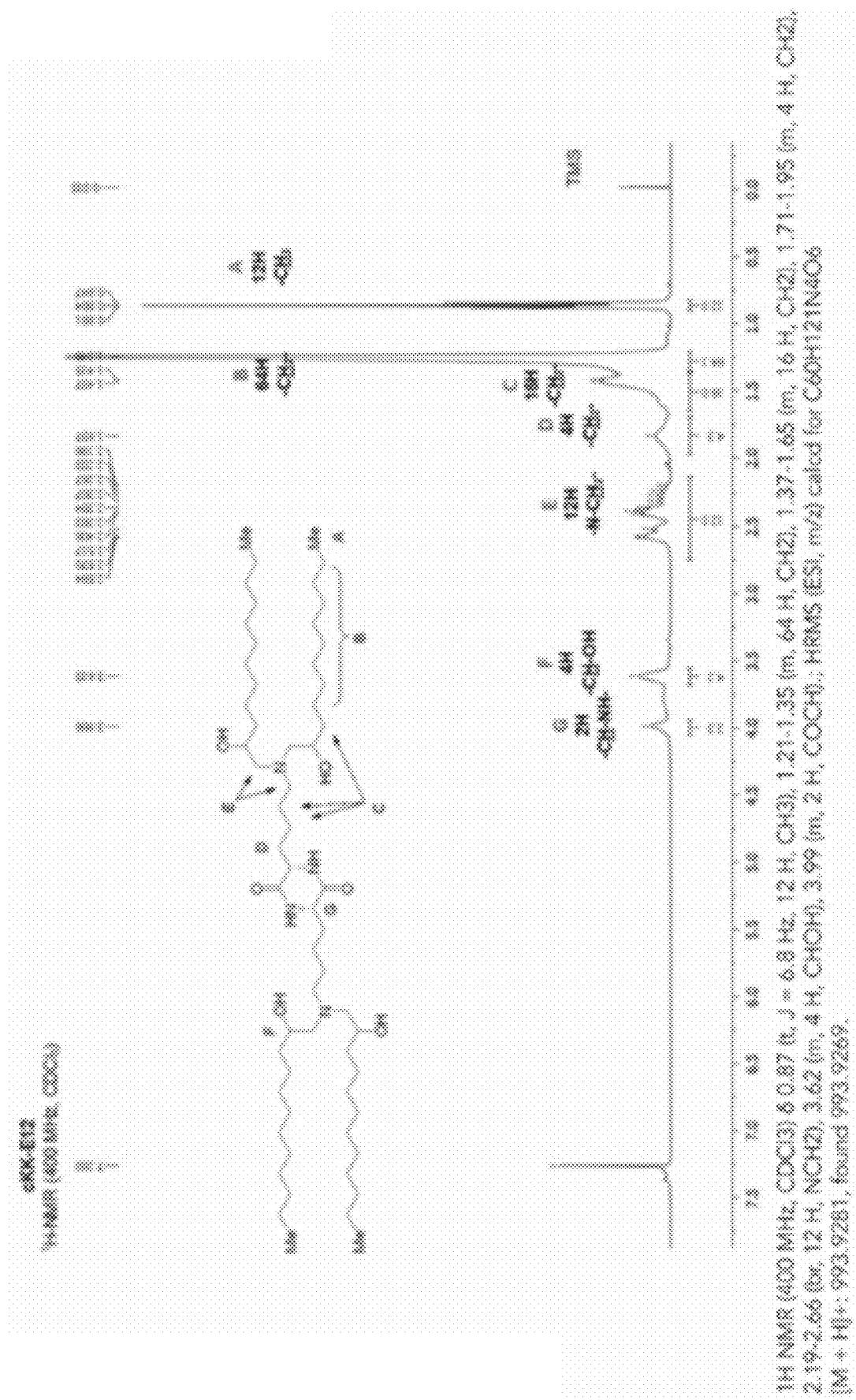
FIG. 6C is an $^1$H-NMR spectra confirming CKK-E12 structure.

Methods:

Synthesis of CKK-E12:

Compound 1 (20 g, 41.9 mmol) was added into a 100 ml flask and trifluoroacetic acid (42 mL) was added slowly at 0° C., then stirred at room temperature for 30 min. The solvent was evaporated under reduced pressure and then the crude product dissolved in DMF (5 mL) was added dropwise to pyridine (300 mL) at 0° C. The reaction mixture was stirred at room temperature overnight. The solvents were evaporated under reduced pressure to afford a white solid and washed with ethyl acetate to give compound 2 (8.4 g, 13.04 mmol, 31% yield) (FIG. 6B). Pd/C (10 wt. %, 3.0 g) was added to a solution of compound 2 in acetic acid/CH2Cl2 (150/150 mL). The black suspension was degassed for 5 min with hydrogen and stirred at room temperature under hydrogen atmosphere overnight. The reaction mixture was filtered by celite and washed with MeOH. The combined filtrates were concentrated to obtain a crude yellow viscous oil. The oil was solidified by adding ethyl acetate and washed with ethyl acetate to yield compound 3 (FIG. 6C). Triethylamine (0.12 mL, 0.88 mmol) was added to a solution of compound 3 (84 mg, 0.22 mmol) and 1,2-epoxydodecane (247 mg, 1.34 mmol) in EtOH (2 mL). After stirring for 30 min at room temperature, the reaction mixture was then irradiated in the microwave reactor at 150° C. for 5 h. Purification of the crude residue via flash column chromatography. After purifying the version with four alkyl tails using flash column chromatography, the chemical structure was confirmed using 1H-NMR (FIG. 6C).

Nanoparticle Formulation:

Nanoparticles were formulated in a microfluidic device by mixing Cre mRNA, DNA, the ionizable lipid, PEG, and cholesterol as previously described (Poisson, et al., *Journal of Hepatology*, 66:212 (2017)). The experimental design can be visualized in FIG. 1H. Nanoparticles were made with variable mole ratios of these constituents. The nucleic acid (e.g. DNA barcode, mRNA) was diluted in 10 mM citrate buffer (Teknova) and loaded into a syringe (Hamilton Company). The materials making up the nanoparticle (CKK-E12, cholesterol, PEG, DOPE) were diluted in ethanol, and loaded into a second syringe. The citrate phase and ethanol phase were mixed together in a microfluidic device using syringe pumps.

DNA Barcoding:

The method of screening and formulating nanoparticles using DNA barcoding is described in PCT/US2018/058171. Each chemically distinct LNP was formulated to carry its own distinct DNA barcode. For example, LNP1 carried Cre mRNA and DNA barcode 1, whereas the chemically distinct LNP2 carried Cre mRNA and DNA barcode 2. The DNA barcodes were designed rationally with universal primer sites and a specific 8 nucleotide barcode sequence, similar to what was previously described (Paunovaska, K., et al. *Nano Lett*, 18:2148 (2018)). To ensure equal amplification of each sequence, we included universal forward and reverse primer regions on all barcodes. An 8 nt sequence can generate over $4^8$ (65,536) distinct barcodes.

Nanoparticle Characterization:

LNP hydrodynamic diameter was measured using dynamic light scattering (DLS). LNPs were diluted in sterile 1×PBS to a concentration of ~0.06 µg/mL, and analyzed. LNPs were included if they met 3 criteria: diameter >20 nm, diameter <215 nm, and autocorrelation function with only 1 inflection point. Particles that met these criteria were pooled and dialyzed in 1× phosphate buffered saline (PBS, Invitrogen), and sterile filtered with a 0.22 µm filter.

Animal Experiments:

All animal experiments were performed in accordance with the Georgia Institute of Technology's Institutional Animal Care and Use Committee (IACUC). C57BL/6J (#000664) and Ai14 LSL-Tomato (#007914) mice were purchased from the Jackson Laboratory. In all experiments, mice were aged 5-8 weeks, and N=3-4 mice per group were injected intravenously via the lateral tail vein. The nanoparticle concentration was determined using NanoDrop (Thermo Scientific). Weights for all animals are included in FIGS. 7A-7C.

Cell Isolation & Staining:

In all cases, mice were sacrificed 3 days after administration of LNPs and immediately perfused with 20 mL of 1×PBS through the right atrium. Organs were isolated immediately following perfusion. Tissues were cut, and then placed in a digestive enzyme solution with Collagenase Type I (Sigma Aldrich), Collagenase XI (Sigma Aldrich), and Hyaluronidase (Sigma Aldrich) at 37° C. and 750 rpm for 45 minutes. The digestive enzyme for heart and spleen included Collagenase IV (Sigma Aldrich). Digested tissues were passed through a 70 µm filter and red blood cells were lysed. Cells were stained to identify specific cell populations and sorted using a BD FacsFusion cell sorter. Antibody clones used for staining were: anti-CD31 (390, BioLegend), anti-CD45.2 (104, BioLegend), anti-CD11b (M1/70, BioLegend), anti-CD68 (FA-11, BioLegend), anti-CD3 (17A2, BioLegend), anti-CD19 (6D5, BioLegend), anti-CD34 (SA376A4, BioLegend). Table 1 shows the FACS markers used for each cell and tissue type.

TABLE 1

FACS markers for each cell type.

| Cell Type | Markers | Tissues |
|---|---|---|
| Hepatocyte (H) | CD45−CD31− | V |
| Kupffer Cell (K) | CD45+CD31−CD68+ | V |
| Endothelial (E) | CD45−CD31+ | V, H, L, K, P, M |
| Immune (I) | CD45+CD31−CD11b−/68− | V, H, L, K, P |
| Other (O) | CD45−CD31− | H, L, K, P, M |

TABLE 1-continued

FACS markers for each cell type.

| Cell Type | Markers | Tissues |
|---|---|---|
| HSCs | CD31−CD45+CD34+ | M |
| Macrophage (M) | CD45+CD11b+ | S, H, L, K, P, M |
| T Cell (T) | CD45+CD19−CD3+ | S |
| B Cell (B) | CD45+CD3−CD19+ | S |
| Immune (I) | CD45+CD19−CD3−CD11b− | S |

PCR Amplification:

All samples were amplified and prepared for sequencing using a nested PCR protocol. More specifically, 1 μL of each primer (10 uM Reverse/Forward) were added to 5 μL of Kapa HiFi 2× master mix, 2 μL sterile H2O, and 1 μL DNA template. The second PCR added Nextera XT chemistry, indices, and i5/i7 adapter regions and used the product from 'PCR 1' as template.

Deep Sequencing:

Illumina deep sequencing was performed on Illumina MiniSeq™ using standard protocols suggested by Illumina. The sequencing was conducted in the Georgia Tech Molecular Evolution core.

Data Normalization:

Counts for each particle were normalized to the barcoded LNP mixture injected into mice, as we previously described (Paunovaska, K., et al. *Nano Lett,* 18:2148 (2018)).

Data Analysis:

Sequencing results were processed using a custom python-based tool to extract raw barcode counts for each tissue. These raw counts were then normalized with an R script prior to further analysis. Statistical analyses were done using GraphPad Prism 7. Data is plotted as mean±standard error unless otherwise stated.

Figure 2A:
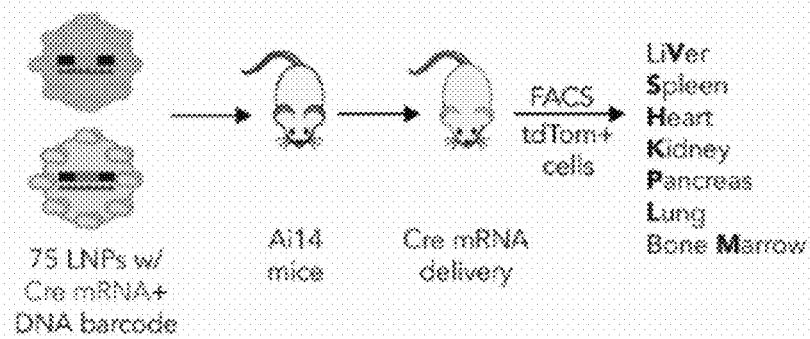
FIG. 2A is an illustration showing the workflow of quantifying mRNA delivery mediated by the disclosed nanoparticles.
Figures 2B, 2C:
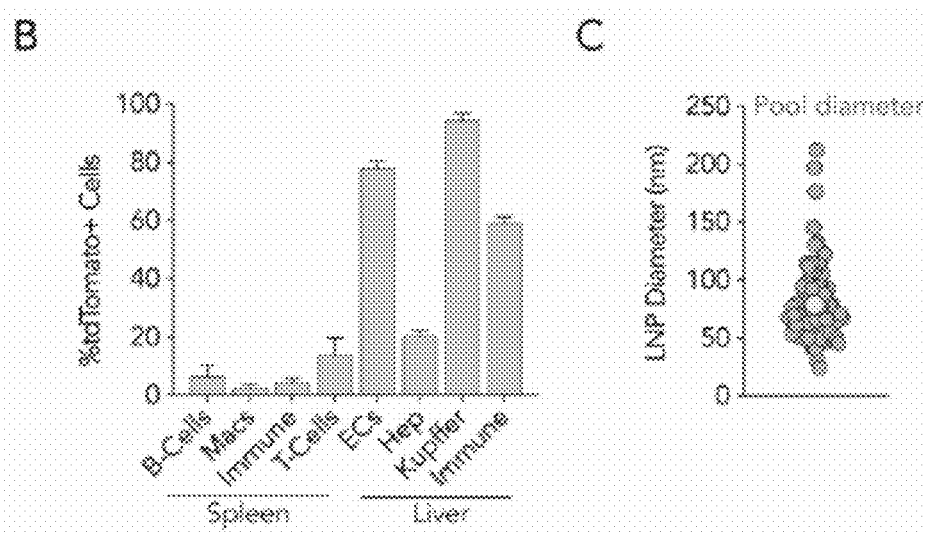
FIG. 2B is a bar graph showing percent tdTomato positive cells in eight cell types from the liver and spleen. The X-axis represents the cell type and the Y-axis represents percent tdTomato+ cells.
FIG. 2C is a scatter dot plot showing the hydrodynamic diameter of all administered lipid nanoparticles.
Figures 2D, 2E:
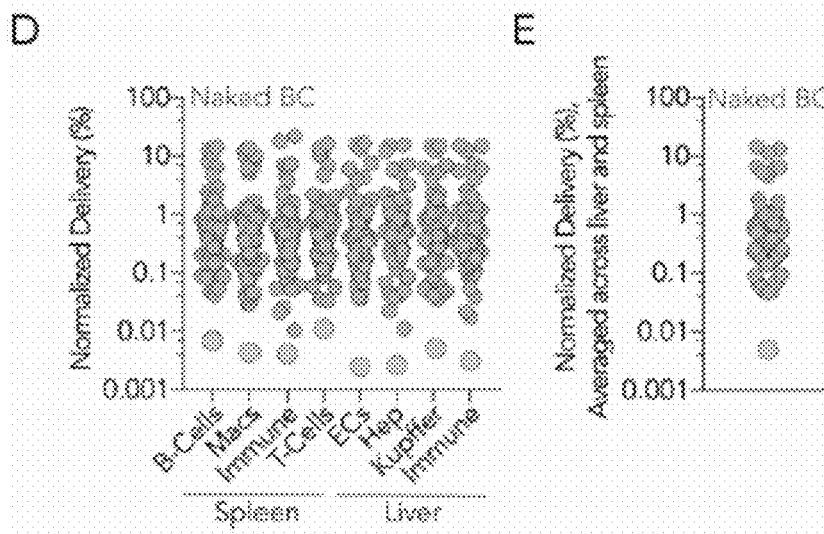
FIG. 2D is a scatter dot plot showing normalized delivery of all administered lipid nanoparticles for eight cell types from the liver and spleen. The X-axis represents the cell type and the Y-axis represents normalized delivery percent.
FIG. 2E shows the normalized delivery for all administered lipid nanoparticles averaged across liver and spleen.
Figure 4A:
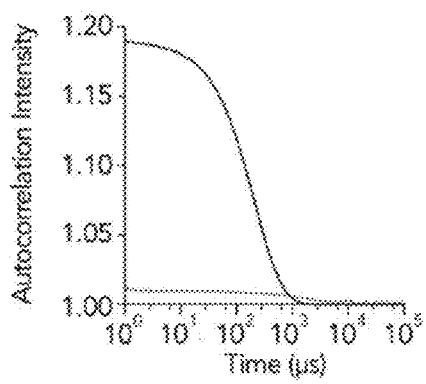
FIG. 4A is a representative autocorrelation curve for included and excluded lipid nanoparticles. The X axis represents time (μs) and the Y axis represents autocorrelation intensity.
Figure 4B:
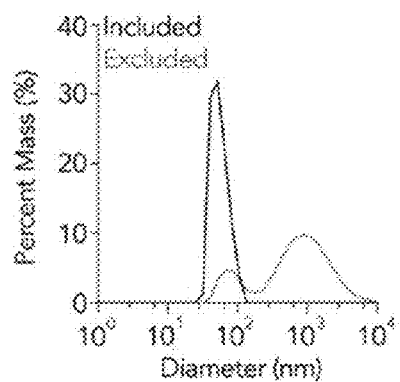
FIG. 4B is a line graph showing diameter distribution for included and excluded lipid nanoparticles. The X axis represents diameter (nm) and the Y axis represents percent mass.

Example 1. Synthesizing a Library of Rationally Designed Nanoparticles Containing Oxidized Cholesterols Results:

As a quality control, the size of each individual LNP was analyzed. LNPs were only pooled if their hydrodynamic diameter was between 20 and 215 nm and their autocorrelation curve contained one inflection point (FIGS. 4A-4B). Eighty-six of the 125 formulated LNPs met these criteria and were pooled. As a control, the diameters of all 86 LNPs were compared to the diameter of the pooled LNP solution, and it was observed that they were similar (FIG. 2C). This suggests that the pooled LNPs did not aggregate after mixing. A naked DNA barcode was added as a negative control since naked DNA does not readily enter cells. After isolating cells and performing NGS, it was determined that—as expected—the naked DNA was delivered into cells less frequently than all the DNA barcodes delivered by LNPs (FIGS. 2D-2E).

Figures 2F, 3A:
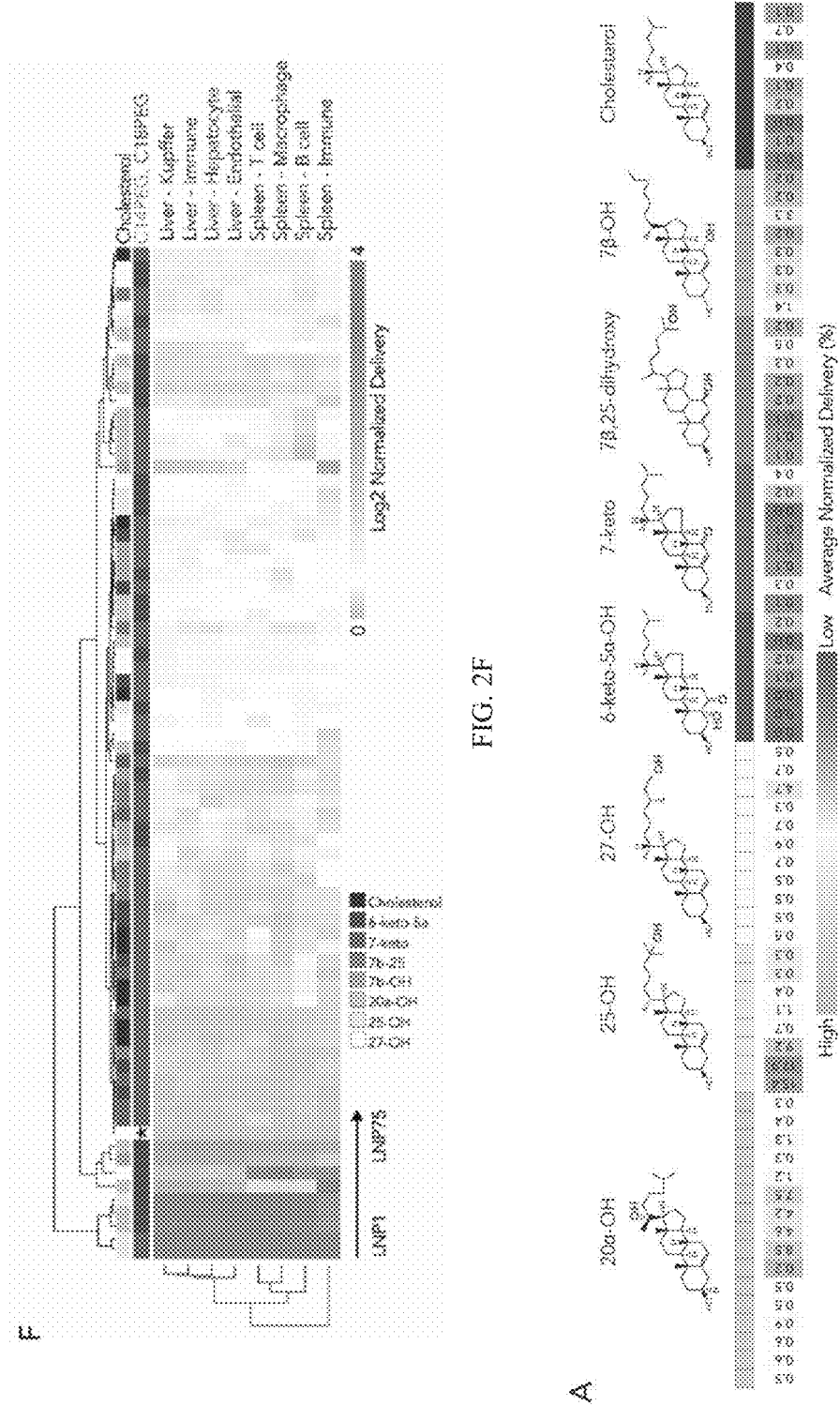
FIG. 2F is an unbiased Euclidean clustering of eight different cell types in two different tissues based on lipid nanoparticle delivery cluster cell types according to tissue. The asterisk represents the naked barcode.
FIG. 3A shows average normalized delivery of lipid nanoparticles sorted by cholesterol type.
Figure 4C:
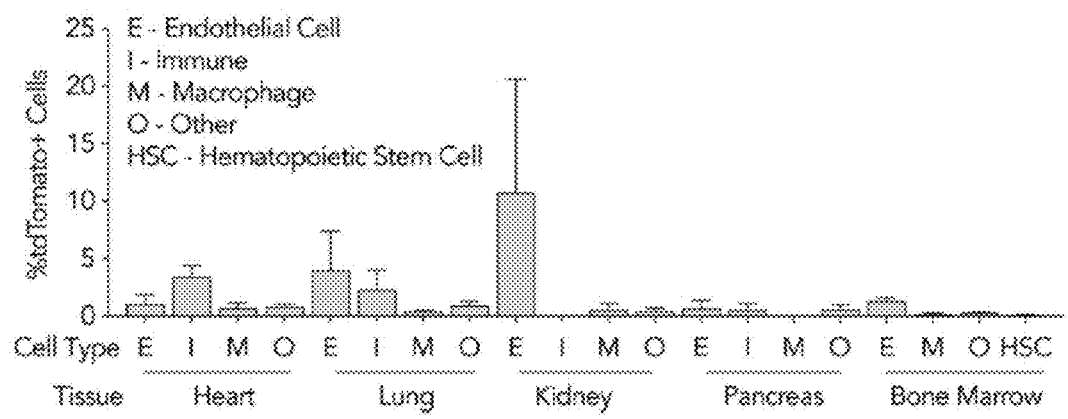
FIG. 4C is a bar graph showing percent tdTomato positive cells for cell types (endothelial cells, E; immune cells, I; macrophage, M; other, O; and hematopoietic stem cell, HSC) isolated from the heart, lung, kidney, pancreas, and bone marrow. The X axis represents cell type and the Y axis represents percent tdTomato+ cells.

Mice were sacrificed 72 hours after injection with the pooled LNPs. This timepoint allows cells to express tdTomato after Cre mRNA delivery (FIG. 2A). The liver, spleen, heart, kidney, pancreas, lung, and bone marrow were then isolated. Using fluorescence activated cell sorting (FACS), 28 different tdTomato+ cell types were isolated (FIG. 2A). Comparing the percentage of tdTomato+ cell types in different organs, cells in the liver tended to be targeted more than cells in other organs (FIG. 2B). The organ with the second-highest percentage of tdTomato+ cells was the spleen. The remaining five organs had negligible delivery (FIG. 4C). The barcode sequencing data was clustered using an unbiased Euclidean algorithm. This bioinformatics technique is regularly applied to gene expression data and can analyze nanoparticle barcoding data. Euclidean clustering revealed that the 4 liver cell types tended to 'cluster' together more closely than they did to splenic cell types (FIG. 2F). It was found that the percentage of tdTomato+hepatic endothelial cells, hepatic immune cells, and Kupffer cells was much higher than the percentage of tdTomato+hepatocytes (FIG. 2B).

Example 2. Modified Cholesterols can Alter Nanoparticle Delivery In Vivo

Methods:

Unmodified cholesterol is acted upon by enzymes to form variants that are side-chain or ring oxidized (FIG. 1A). To investigate whether these modifications altered LNP targeting, 125 LNPs were formulated using microfluidics (FIG. 1B-1G). To minimize variation from components other than cholesterol, LNPs were made of the ionizable lipid-like material cKK-E12, two well validated PEG-lipids, the phospholipid 1,2-Dioleoyl-sn-glycero-3-phosphoethanolamine (DOPE), and one of nine different cholesterol variants (FIG. 1B-1G).

Figure 1H:
FIG. 1H is an illustration showing the workflow of barcoding the disclosed nanoparticles.
Figure 1I:
FIG. 1I is an illustration showing the workflow of testing the disclosed nanoparticles.

LNPs were formed by mixing the contents together in a microfluidic device. Each LNP carried a unique DNA barcode, which acted as a tag for that LNP, as well as Cre mRNA, which signals functional mRNA delivery (FIG. 1H). Stable LNPs were pooled together (FIG. 1I) and administered to Ai14 mice at a total nucleic acid dose of 1.0 mg/kg. Ai 14 mice contain a Lox-Stop-Lox-tdTomato construct under the control of a CAG promoter; as a result, cells in Ai14 mice become tdTomato+ if: (1) Cre mRNA is delivered into the cytoplasm, (2) Cre mRNA is translated into Cre protein, (3) Cre protein translocates from the cytoplasm into the nucleus, and (4) Cre protein edits the genome by removing the 'Stop' between Lox sites. Therefore, by isolating tdTomato+ cell types using fluorescence-activated cell sorting (FACS) and using next generation sequencing (NGS) to quantify barcodes within them, LNPs located in cells where functional mRNA delivery occurred can be identified (FIG. 1I). NGS sequencing data was quantified as 'normalized delivery', analogous to counts per million in RNA-seq (FIG. 1I).

Figures 3B, 3C, 3D:
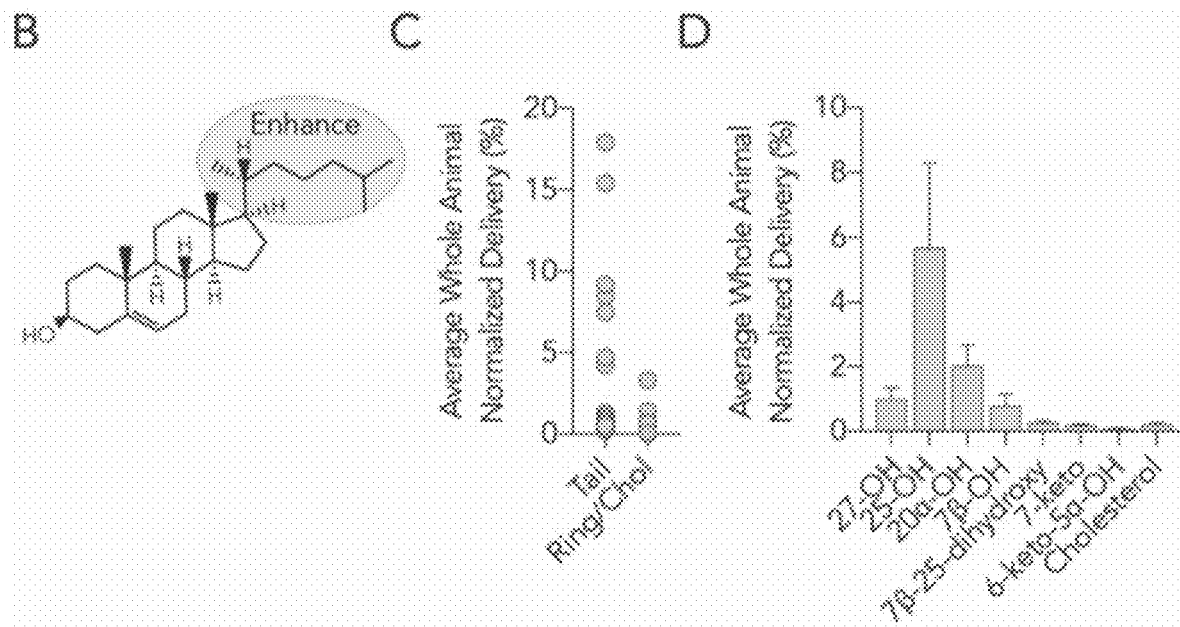
FIG. 3B shows the chemical structure of cholesterol with modifications on the cholesterol tail.
FIG. 3C is a dot plot showing normalized delivery averaged across all eight liver and spleen cell types for lipid nanoparticles with cholesterols with modifications on the cholesterol tail (tail) and cholesterols with modifications to the B ring (Ring/Chol).
FIG. 3D is a bar graph showing normalized delivery averaged across all eight liver and spleen cell types for lipid nanoparticles with different cholesterols including 27-OH, 25-OH, 20α-OH, 7β-OH, 7β-OH, 7β-25-dihydroxy, 7-keto, 6-keto-5α-OH, and cholesterol. The X-axis represents the type of cholesterol in the lipid nanoparticles and the Y-axis represents average whole animal normalized delivery.
Figures 3E, 3F:
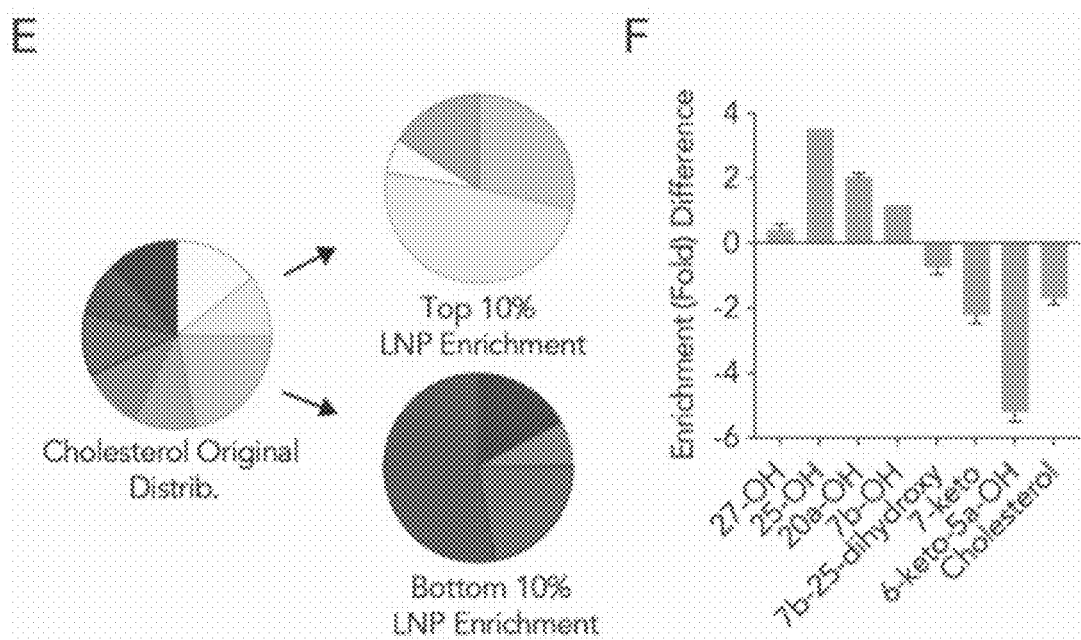
FIG. 3E is an illustration showing enrichment of cholesterol variants in the top 10% and bottom 10% of lipid nanoparticles.
FIG. 3F is a bar graph showing fold enrichment in the top 10% of lipid nanoparticles, calculated by subtracting enrichment in the bottom 10% of lipid nanoparticles from enrichment in the top 10% of lipid nanoparticles.
Figures 3G, 3H, 3I, 3J:
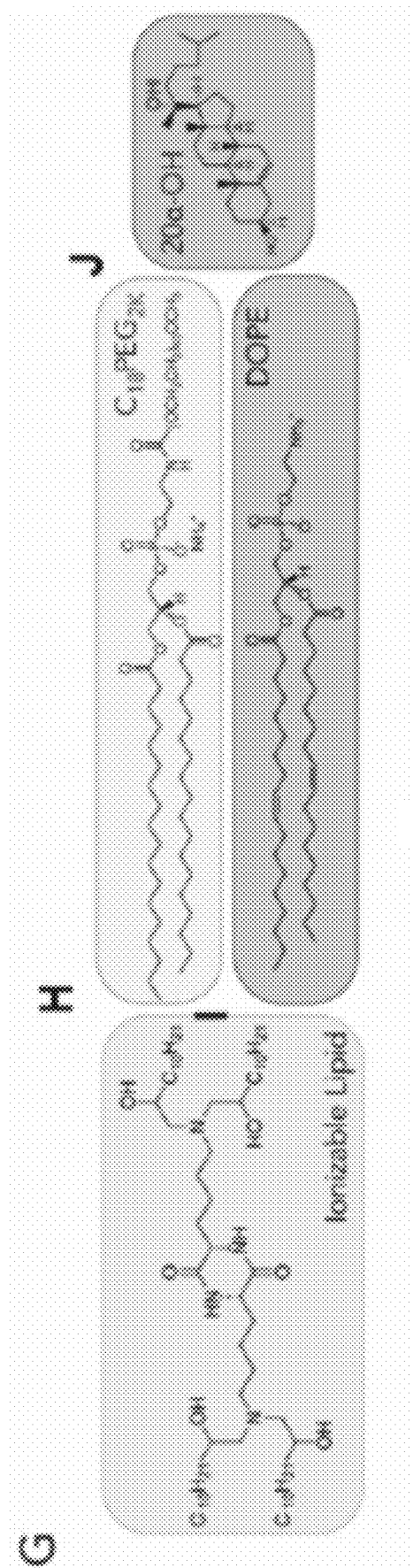
FIG. 3G is the chemical structure of ionizable lipid cKK-E12.
FIG. 3H is the chemical structure of $C_{18}PEG_{2000}$.
FIG. 3I is the chemical structure of DOPE.
FIG. 3J is the chemical structure of 20α-OH.
Figure 3K:
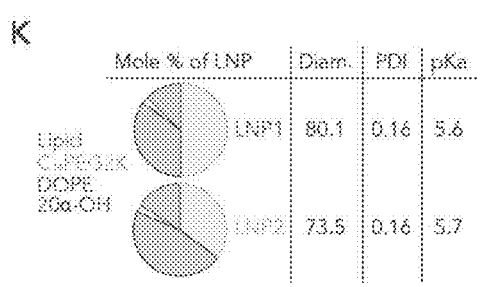
FIG. 3K is a diagram showing the lipid nanoparticle molar percent of each component of the two formulations, the diameter, polydispersity (PDI), and pKa of the lipid nanoparticles.
Figures 3L, 3M, 3N, 3O:
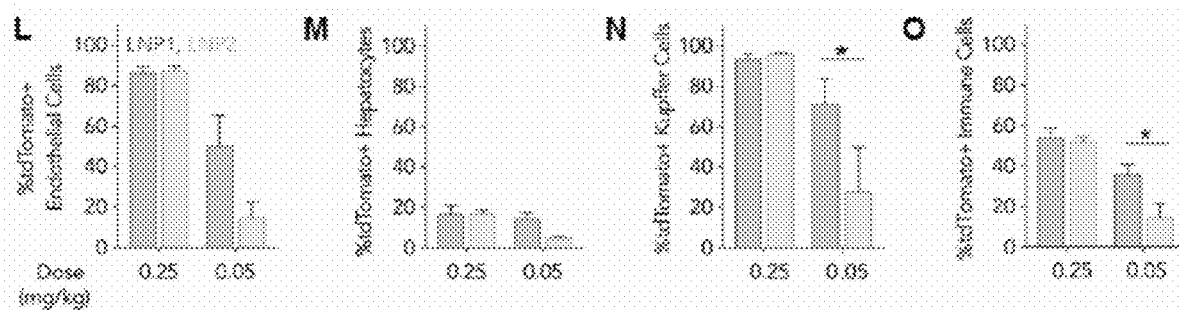
FIGS. 3L-3O are bar graphs showing the percent tdTomato positive endothelial cells (FIG. 3L), hepatocytes (FIG. 3M), Kupffer cells (FIG. 3N), and immune cells (FIG. 3O) in mice administered 0.25 mg/kg or 50 mg/kg LNP1 or LNP2. The X-axis represents lipid nanoparticle dose and the Y-axis represents percent tdTomato+ cells.
Figure 5A:
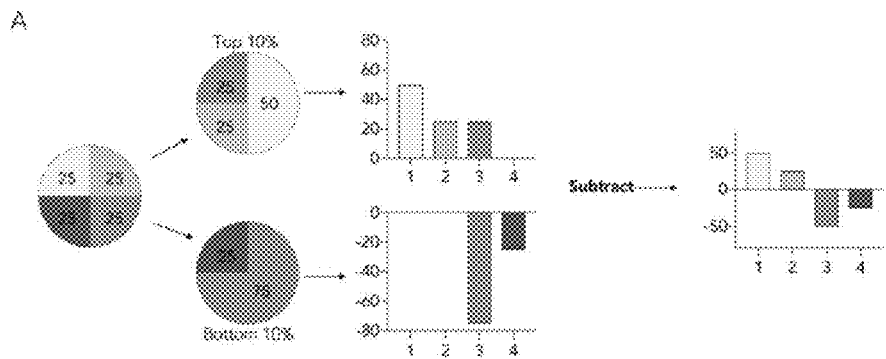
FIG. 5A is a diagram showing enrichment calculations for obtaining enrichment (fold) difference values, average whole animal normalized delivery (%), and enrichment in the top and bottom 10% of lipid nanoparticles.
Figures 5B, 5C, 5D:
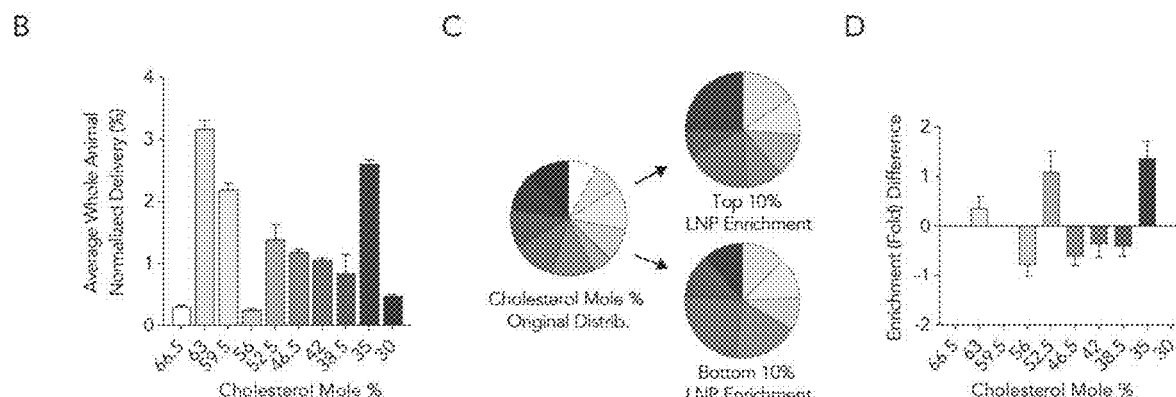
FIGS. 5B-5D show fold difference in enrichment for cholesterol mole %.
Figures 5E, 5F, 5G:
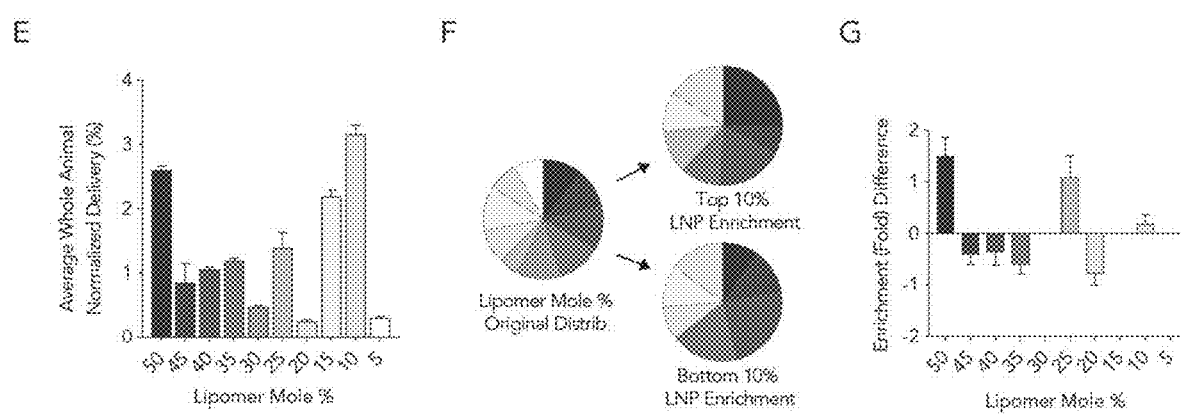
FIGS. 5E-5G show fold difference in enrichment for ionizable lipid mole %.
Figures 5H, 5I, 5J:
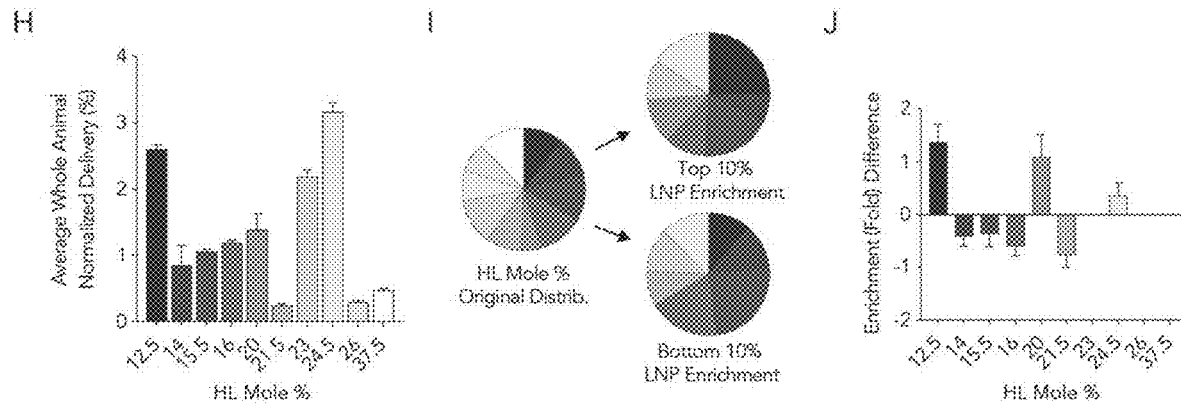
FIGS. 5H-5J show fold difference in enrichment for phospholipid mole %.

Results:

To quantify the impact of cholesterol structure on overall splenic and hepatic delivery, we calculated the normalized delivery for all 8 cell types we sequenced (4 in spleen and 4 in liver) (FIG. 3A). Side-chain oxidized cholesterol variants tended to enhance delivery relative to the other cholesterol variants (FIG. 3B-3C). In particular, LNPs formulated with 25-hydroxycholesterol (25-OH) and 20α-hydroxycholesterol (20α-OH) resulted in higher normalized delivery across all 8 cell types (FIG. 3D). To complement these calculations, it was determined which cholesterol variants were enriched in the top 10% of LNPs (FIG. 3E). The enrichment in the bottom 10% of LNPs was then calculated and subtracted from enrichment in the top 10% (FIG. 3E-3F). This identifies how likely it is that a given cholesterol variant is found in the best- and worst performing LNPs. Enrichment calculations are detailed in FIG. 5A. As an additional control, the same two analyses were performed—normalized delivery across all 8 cell types, and enrichment—for cholesterol mole percentage, ionizable lipid mole percentage, and phospholipid mole percentage (FIG. 5B-5D). No significant trends were observed.

Figures 5K, 5L, 5M:
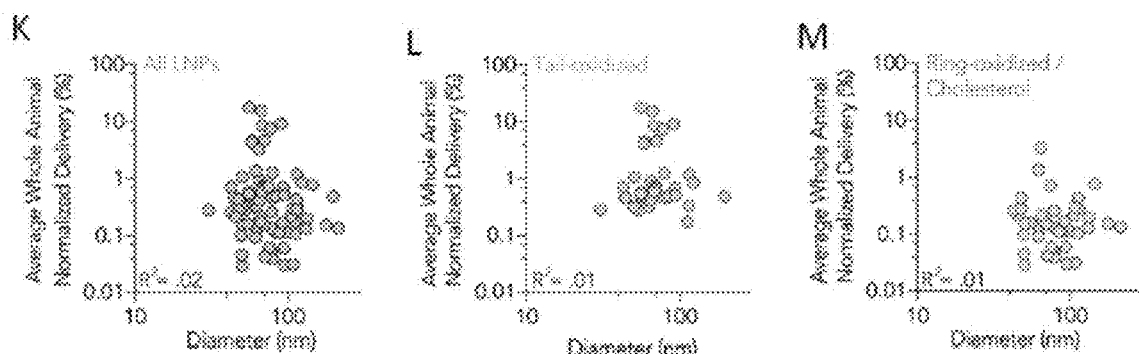
FIGS. 5K-5M are dot plots showing lipid nanoparticle diameter plotted against average whole animal normalized delivery for all lipid nanoparticles (FIG. 5K), lipid nanoparticles containing only tail-modified cholesterols (FIG. 5L), and lipid nanoparticles containing ring-oxidized cholesterols (FIG. 5M).
Figures 5N, 5O:
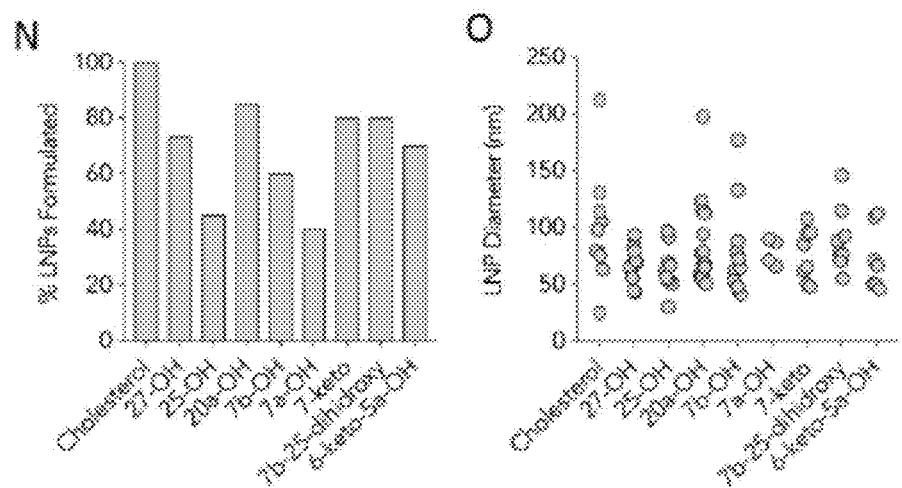
FIGS. 5N and 5P are bar graphs showing percent of lipid nanoparticles formed based on cholesterol variant used (FIG. 5N) and cholesterol mole % (FIG. 5P).
FIGS. 5O and 5Q are dot plots showing lipid nanoparticle diameter based on cholesterol variant used (FIG. 5O) and cholesterol mole % (FIG. 5Q).
Figures 5P, 5Q:
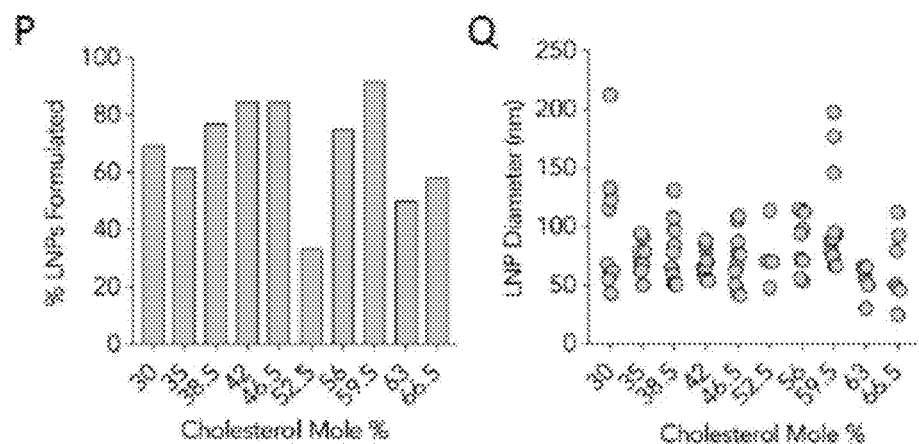

These data suggested that LNP cholesterol chemical composition was an important factor in LNP targeting. However, it did not take LNP size into account. It was previously found that there was no relationship between nanoparticle size and delivery for hydrodynamic diameters between ~20 and ~200 nm. To investigate how size altered delivery in this experiment, it was calculated whether normalized delivery varied with LNP size for all LNPs (FIG. 5K), LNPs with tail oxidized cholesterols (FIG. 5L), and LNPs with ring oxidized cholesterols (FIG. 5M); no relationship was found. The percentage of formulated LNPs that met the inclusion criteria as a function of cholesterol structure and the average size of stable LNPs based on cholesterol structure were calculated. No significant differences were found (FIG. 5N-5O). The same analyses were performed as a function of cholesterol mole percentage, and the same conclusions were reached (FIG. 5P-5Q). Thus, there was no evidence that size affected LNP delivery between 20 and 215 nm.

Figures 7A, 7B, 7C, 7D:
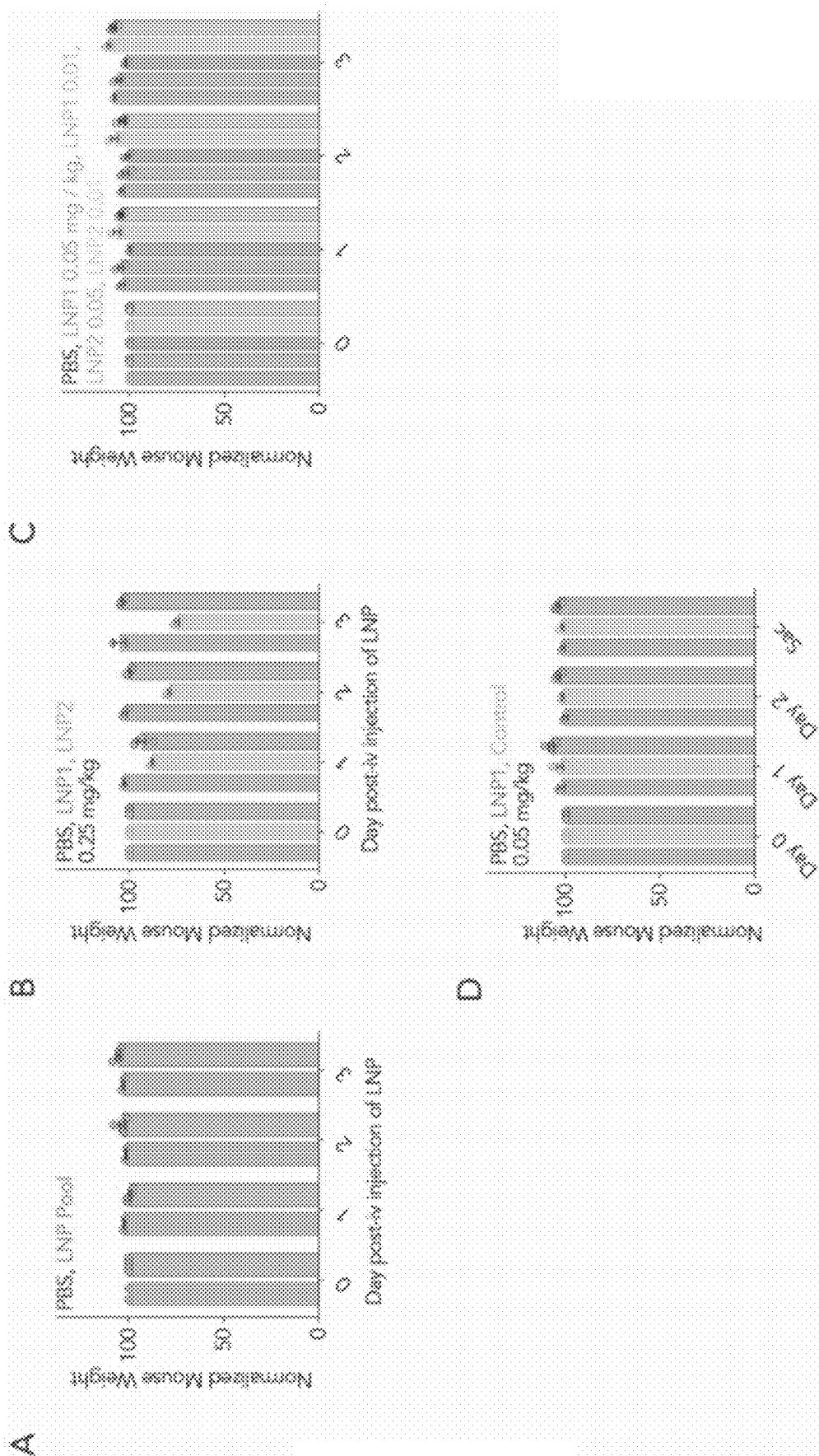
FIGS. 7A-7D are bar graphs showing body weight for mice injected with 1 mg/kg lipid nanoparticle pool (FIG. 7A), LNP1 and LNP2 containing cre mRNA at a dose of 0.25 mg/kg (FIG. 7B), LNP1 and LNP2 containing cre mRNA at a dose of 0.05 mg/kg and 0.01 mg/kg, and LNP1 containing cre mRNA at a dose of 0.05 mg/kg compared to control (FIG. 7D). The X axis represents days post-iv injection of lipid nanoparticles and the Y axis represents normalized mouse body weight. PBS injections were used as a control.

To this end, the top 3 LNP candidates identified were formulated with Cre mRNA. Of the 3 LNPs formulated, one LNP—which contained 25-OH cholesterol—did not formulate consistently and was excluded. The remaining two LNPs—which contained 20α-OH cholesterol (FIG. 3G-3K)—formed stable LNPs, and were administered to Ai14 mice at a total mRNA dose of 0.25 mg/kg. Encouragingly, both LNPs recapitulated the results from an earlier screen (FIG. 3L-3O). Both LNP1 and LNP2 robustly targeted cells in the microenvironment after a 0.25 mg/kg injection. As predicted by the screen, hepatocytes were targeted far less efficiently. Encouraged by robust delivery at 0.25 mg/kg, LNP1 and LNP2 were injected at a dose of 0.05 mg/kg. Once again, robust delivery was observed (FIG. 3L-3O). Whereas LNP1 and LNP2 both performed equally well at 0.25 mg/kg by saturating the Cre-based system, LNP1 outperformed LNP2 at the lower dose of 0.05 mg/kg. LNP1 did not cause mouse weight loss in any experiment; LNP2 did cause mice to lose weight at 0.25 mg/kg (FIGS. 7A-7C).

Systemic delivery of therapeutic RNA to hepatocytes has led to an FDA approved drug (Rizk, M and Tuzmen, S., *Pharmacogenomics and Personalized Medicine*, 10:267 (2017)). Delivery to non-hepatocytes has remained more challenging. Thus, an unbiased, high throughput method to study how LNPs deliver RNA in vivo could accelerate the discovery of nanoparticles with new tropisms. Here it is reported that LNPs containing oxidized cholesterol can deliver mRNA to cells in the liver microenvironment more potently than to hepatocytes. Notably, robust delivery occurred at 0.05 mg/kg, which is below the dose regime used for siRNA therapies in humans. Given the importance of liver endothelial cells (Poisson, et al., *Journal of Hepatology*, 66:212 (2017)) and Kupffer cells (Kolios, G., et al., *World Journal of Gastroenterology*, 12:7413 (2006)) in disease, these data suggest that additional advances in delivery could eventually result in protein replacement therapies within the liver microenvironment.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A lipid nanoparticle composition comprising,
    an ionizable lipid,
    a phospholipid,
    a polyethylene glycol (PEG), and
    a side-chain oxidized cholesterol;
    wherein the ionizable lipid, the phospholipid, the polyethylene glycol and the side-chain oxidized cholesterol are all selected together in combination to provide the lipid nanoparticle composition with a capability to more potently deliver a cargo that is encapsulated within the nanoparticle to non-hepatocytes than to hepatocytes in a liver microenvironment.

2. The nanoparticle composition of claim 1, wherein the ionizable lipid is 3,6-bis({4-[bis(2-hydroxydodecyl)amino]-butyl})piperazine-2,5-dione (CKK-E12).

3. The nanoparticle composition of claim 1, wherein the phospholipid is 1,2-Dioleoyl-sn-glycero-3-phosphoethanolamine (DOPE).

4. The nanoparticle composition of claim 1, wherein the PEG is $C_{14}PEG_{2000}$ or $C_{18}PEG_{2000}$.

5. The nanoparticle composition of claim 1, wherein the oxidized cholesterol is selected from the group consisting of 20α-hydroxycholesterol, 7β,25-dihydroxylcholesterol, 27-hydroxycholesterol, and 25-hydroxycholesterol, or combinations thereof.

6. The nanoparticle composition of claim 1, wherein the composition comprises about 30 mol % to about 80 mol % ionizable lipid, about 5 mol % to about 55 mol % side-chain oxidized cholesterol, about 10 mol % to about 35 mol % phospholipid, and about 0 mol % to about 20 mol % PEG-lipid.

7. The nanoparticle composition of claim 1, further comprising a therapeutic or prophylactic agent.

8. The nanoparticle composition of claim 7, wherein the therapeutic or prophylactic agent is encapsulated as the cargo within the lipid nanoparticle.

9. The nanoparticle composition of claim 7, wherein the therapeutic or prophylactic agent is a ribonucleic acid (RNA).

10. The nanoparticle composition of claim 9, wherein the RNA is messenger RNA (mRNA).

11. The nanoparticle composition of claim 1, wherein the nanoparticle has a diameter from about 20 nm to about 215 nm.

12. A pharmaceutical composition comprising the lipid nanoparticles of claim 1, and a pharmaceutically acceptable excipient.

13. The lipid nanoparticle composition of claim 1, wherein
    the ionizable lipid is CKK-E12,
    the phospholipid is DOPE,
    the polyethylene glycol (PEG) is $C_{18}PEG_{2000}$, and
    the side chain oxidized cholesterol is 20α-hydroxycholesterol.

14. The lipid nanoparticle composition of claim 1, wherein
    the ionizable lipid is CKK-E12,
    the phospholipid is DOPE,
    the polyethylene glycol (PEG) is $C_{18}PEG_{2000}$, and
    the side chain oxidized cholesterol is 25-hydroxycholesterol.

15. A method of delivering a therapeutic or prophylactic agent to a subject in need thereof, comprising, administering to the subject the lipid nanoparticle composition of claim 7.

16. A method of preventing or treating liver disease in a subject in need thereof, comprising, administering to the subject the lipid nanoparticle of claim 1 in an amount effective to prevent or treat liver disease.

17. A method for delivering a drug to Kupffer cells of a subject in need thereof, comprising:
  administering the lipid nanoparticles of claim 7 in an amount effective to deliver the drug to the Kupffer cells.

18. A method for delivering a drug to liver endothelial cells of a subject in need thereof, comprising:
  administering the lipid nanoparticles of claim 7 in an amount effective to deliver the drug to the liver endothelial cells.

19. A method for delivering a drug to immune cells of a subject in need thereof, comprising:
  administering the lipid nanoparticles of claim 7 in an amount effective to deliver the drug to the liver endothelial cells.

* * * * *